(12) United States Patent
Lee

(10) Patent No.: US 11,660,615 B2
(45) Date of Patent: May 30, 2023

(54) CENTRIFUGAL SEPARATION CONTAINER, AND METHOD FOR MOVING SUBSTANCES INSIDE CENTRIFUGAL SEPARATION CONTAINER

(71) Applicant: Jun Seok Lee, Busan (KR)

(72) Inventor: Jun Seok Lee, Busan (KR)

( * ) Notice: Subject to any disclaimer, the term of this patent is extended or adjusted under 35 U.S.C. 154(b) by 802 days.

(21) Appl. No.: 16/319,745

(22) PCT Filed: Jul. 18, 2017

(86) PCT No.: PCT/KR2017/007740
§ 371 (c)(1),
(2) Date: Jan. 22, 2019

(87) PCT Pub. No.: WO2018/016858
PCT Pub. Date: Jan. 25, 2018

(65) Prior Publication Data
US 2019/0336985 A1 Nov. 7, 2019

(30) Foreign Application Priority Data

Jul. 19, 2016 (KR) .................. 10-2016-0091523

(51) Int. Cl.
*B04B 11/06* (2006.01)
*B04B 11/05* (2006.01)
(Continued)

(52) U.S. Cl.
CPC .............. *B04B 11/06* (2013.01); *B04B 11/05* (2013.01); *A61M 1/3696* (2014.02);
(Continued)

(58) Field of Classification Search
CPC ....... B04B 11/06; B04B 11/05; B04B 5/0421; B04B 5/0442; B04B 2005/0485;
(Continued)

(56) References Cited

U.S. PATENT DOCUMENTS 3,800,947 A * 4/1974 Smith ................... B01L 3/5021
422/918
4,904,284 A 2/1990 Hanabusa
(Continued)

FOREIGN PATENT DOCUMENTS

EP 3025788 A1 1/2016
EP 3124121 A1 2/2017
(Continued)

OTHER PUBLICATIONS

JP 2010099616 Description Espacenet English machine translation.*
(Continued)

*Primary Examiner* — Shuyi S. Liu
(74) *Attorney, Agent, or Firm* — Schwabe Williamson & Wyatt

(57) ABSTRACT

Provided is a centrifugal separation container for separating a material from tissue and body fluids by using a centrifugal force, including: a first container; a second container; a first piston positioned in the inside of the first container and configured to be movable up and down in the inside of the first container; an elastic body positioned below the first piston in the inside of the first container and configured to elastically bias the first piston upward; a first connecting duct having one end connected to the first container and the other end connected to the second container; and a first control valve operating by a centrifugal force and configured to open and close the first connecting duct.

11 Claims, 34 Drawing Sheets

(51) Int. Cl.
A61M 1/36 (2006.01)
B01L 3/00 (2006.01)

(52) U.S. Cl.
CPC ..... *B01L 3/5021* (2013.01); *B01L 2300/0851* (2013.01); *B01L 2300/0858* (2013.01); *B01L 2400/0409* (2013.01)

(58) Field of Classification Search
CPC ............... A61M 1/3696; B01L 3/5021; B01L 2300/0851; B01L 2300/0858; B01L 2400/0409; B01L 3/502738; B01L 3/50273; B01L 2400/0633; B01L 2400/0478; B01L 2300/0854; F16K 99/0063; F16K 99/0026
USPC .................................................. 494/4, 16, 20
See application file for complete search history.

(56) References Cited

U.S. PATENT DOCUMENTS

| | | | | |
|---|---|---|---|---|
| 5,171,532 | A | * | 12/1992 | Columbus ........ G01N 35/00029 422/536 |
| 2009/0209402 | A1 | | 8/2009 | Andersson |
| 2013/0226150 | A1 | | 8/2013 | Nash et al. |
| 2014/0370499 | A1 | * | 12/2014 | Hoang .................. G01N 1/286 435/6.1 |
| 2016/0209409 | A1 | * | 7/2016 | Choi ........................ B03C 1/01 |

FOREIGN PATENT DOCUMENTS

| | | | | | |
|---|---|---|---|---|---|
| JP | 2005013783 | A | | 1/2005 | |
| JP | 3137413 | U | * | 11/2007 | |
| JP | 3137413 | U | | 11/2007 | |
| JP | 2010099616 | A | * | 5/2010 | |
| JP | 2010099616 | A | | 5/2010 | |
| KR | 20120092934 | A | | 8/2012 | |
| KR | 101390247 | B1 | | 4/2014 | |
| KR | 101466762 | B1 | | 11/2014 | |
| WO | WO-2007126357 | A1 | * | 11/2007 | ........... B04B 5/0442 |
| WO | 2015147606 | A1 | | 10/2015 | |
| WO | WO-2015147606 | A1 | * | 10/2015 | ............ B01L 3/5021 |

OTHER PUBLICATIONS

JP 3137413 Description Espacenet English machine translation.*
Korean Intellectual Property Office, Office Action for Korean Patent Application No. 10-2016-0091523, dated Nov. 20, 2017, 6 pages, no English translation available.
Korean Intellectual Property Office, Notice of Allowance for Korean Patent Application No. 10-2016-0091523, dated Oct. 29, 2018, 2 pages, no English translation available.
Korean Intellectual Property Office International Search Report and Written Opinion of the International Searching Authority, dated Oct. 26, 2017, 15 pages.
Partial European Search Report from European Patent Application No. 17831331.8 dated Apr. 1, 2020, 17 pgs.

* cited by examiner (a)

(b)

(a) 437

437

438 (b)

(a)　　　　　　　　　　(b)

(a)                (b)

CENTRIFUGAL SEPARATION CONTAINER, AND METHOD FOR MOVING SUBSTANCES INSIDE CENTRIFUGAL SEPARATION CONTAINER

TECHNICAL FIELD

The present disclosure relates to a centrifugal separation container, and a method for moving substances inside the centrifugal separation container, and more particularly, to a centrifugal separation container capable of easily separating cells or specific materials from tissue, blood fluids, etc., injecting materials, discharging discharge target materials, and extracting and washing extracts, and a method of moving substances in the centrifugal separation container.

BACKGROUND ART

Centrifugal separators are used to separate specific cells, materials, etc. from tissue such as fatty tissue or body fluids such as blood, bone marrow, etc. The centrifugal separators, which are apparatuses for separating cells, materials, etc. from tissue and body fluids by using a centrifugal force, are in use widely since they can easily separate materials through a simple configuration and easy operations.

The centrifugal separators use a centrifugal separation container that accommodates specific tissue and body fluids and is rotatably configured to perform centrifugation. In the centrifugal separation container, tissue and body fluids are accommodated, and when it rotates on a predetermined rotation shaft, materials in the tissue and body fluids are separated by a centrifugal force.

However, typical centrifugal separation containers have problems that tissue, fluids, etc. injected in the containers flow backward during centrifugation, that it is difficult to connect discharging means to the containers in a discharge process, or that extracts remain in the containers after separated materials are extracted. Also, the typical containers require long container paths for injecting and discharging materials, movement target materials, etc. and have a problem that it is not easy to inject and discharge movement target materials for washing extracts. Accordingly, the typical containers may have difficulties in obtaining high-purity extracts.

DESCRIPTION OF EMBODIMENTS

Technical Problem

Provided are a centrifugal separation container capable of easily injecting tissue, body fluids, etc., discharging discharge target materials, and extracting and washing extracts, and a method for moving materials in the centrifugal separation container.

Solution to Problem

According to an aspect of the present disclosure, there is provided a centrifugal separation container for separating a material from tissue and body fluids by using a centrifugal force, including: a first container; a second container; a first piston positioned in the inside of the first container and configured to be movable up and down in the inside of the first container; an elastic body positioned below the first piston in the inside of the first container and configured to elastically bias the first piston upward; a first connecting duct having one end connected to the first container and the other end connected to the second container; and a first control valve operating by a centrifugal force and configured to open and close the first connecting duct.

Preferably, the centrifugal force may have a component for moving the first piston downward.

Preferably, the first control valve may include at least one of: a first valve configured as an initial close valve that is closed before a centrifugal force is applied and that is opened after a centrifugal force is applied; and a second valve configured as a normal open valve that is opened when no centrifugal force is applied and that is closed when a centrifugal force is applied.

Preferably, at least one part of the first connecting duct may be made of a material having elasticity to be deformable by an external force.

Preferably, the first valve may include: a first valve body made of a material having a predetermined weight; and a first rotation shaft to which the first valve body is rotatably connected, the first rotation shaft spaced from a center of gravity of the first valve body, wherein at least one part of the first valve body is caught between the first connecting duct and the first rotation shaft and fixed while pressing and deforming at least one part of the first connecting duct to close the first connecting duct, and when a centrifugal force is applied to the first valve body, the first valve body rotates on the first rotation shaft to restore the first connecting duct.

Preferably, the second valve may include: a second valve body made of a material having a predetermined weight; and a second rotation shaft to which the second valve body is rotatably connected, the second rotation shaft spaced from a center of gravity of the second valve body, wherein, when a centrifugal force is applied to the second valve body, the second valve body rotates on the second rotation shaft to press and deform at least one part of the first connecting duct to close the first connecting duct.

Preferably, the first connecting duct may include a first duct connected to the first container, a second duct connected to the second container, and a vertical flow path connecting the first duct to the second duct and extending vertically, wherein the first control valve comprises a weight body having a predetermined weight and an elastic ring disposed around the weight body, and is friction-fitted in the vertical flow path.

Preferably, a valve operating hole may be formed above the vertical flow path to extend vertically, and an operating beam may be connected to a top end of the weight body to pass the valve operating hole to be exposed upward.

Preferably, the centrifugal separation container may further include a stopper formed in the shape of a predetermined block and having a groove into which the operating beam is inserted, the stopper being detachable from the operating beam, wherein a predetermined support step is provided at a top end of the operating beam, and by inserting the operating beam into the groove to support the support step by the stopper from below, a position of the weight body is fixed.

Preferably, at least one part of the first connecting duct may be made of a material having elasticity to be deformable by an external force, and the first control valve may include a rotation valve, wherein the rotation valve may include: a valve hammer including a valve rod having a predetermined length, a pressing head formed at one end of the valve rod, located above the first connecting duct, and having a predetermined weight, and a rotation shaft disposed at the other end of the valve rod, the valve hammer configured to be rotatable on the rotation shaft; and a valve elastic member configured to elastically bias the pressing head upward.

Preferably, the centrifugal separation container may further include: a third container; a second piston positioned in the inside of the third container and configured to be movable up and down in the inside of the third container; and a second connecting duct connecting the third container with the first container.

Preferably, the centrifugal separation container may further include a second control valve configured to open and close the second connecting duct, wherein the second connecting duct may include a first line and a second line, the third container may have an entrance hole formed above the second piston, the second piston may be in close contact with an inner side surface of the third container, have a predetermined weight, and have a vertical through hole penetrating the second piston body vertically, the first line may pass through the entrance hole and has one end connected to the second control valve and the other end connected to the vertical through hole, and the second line may have one end connected to the second control valve and the other end connected to the first container.

Preferably, the second piston may further include a weight body having a predetermined weight.

According to an aspect of the present disclosure, there is provided a method for moving a material in a centrifugal separation container, the centrifugal separation container including: a first container having a first space; a first piston positioned in the first space, dividing the first space to an upper space and a lower space, and configured to be movable up and down in the inside of the first container; a filling container having a filling space in which a movement target material is filled; a second piston positioned in the inside of the filling container, dividing the filling space into an upper space and a lower space, and configured to be movable up and down in the inside of the filling container; and a connecting duct connecting the first container to the filling container, and having one end connected to the lower space below the second piston in the filling container and the other end connected to the upper space above the first piston in the first container, wherein a centrifugal force may be applied to move the second piston and the first piston downward, and positive pressure generated by the second piston may be combined with negative pressure generated by the first piston so that a material filled below the second piston in the filling container may move to the upper space above the first piston in the first container through the connecting duct.

Advantageous Effects of Disclosure

The centrifugal separation container according to the present disclosure may include the first control valve configured as a centrifugal valve to easily inject, separate and discharge materials, and to easily wash extracts, thereby easily collecting high-purity extracts.

According to an embodiment, the first control valve may include at least one of an initial close valve and a normal open valve that are properly opened or closed during operations of injecting, separating, and discharging materials and of washing extracts.

Also, according to an embodiment, by providing the second and third containers such that the first, second, and third containers are respectively in charge of separating materials, discharging materials, and injecting movement target materials, the centrifugal separation container may have a simple, compact, and advantageous structure, and keep balance.

In the coupling structure of the centrifugal separation container according to the present disclosure, the plurality of centrifugal separation containers may be arranged symmetrically to the center shaft to keep total weight balance.

The method of moving a material in the centrifugal separation container may easily move a material by using a centrifugal force in a centrifugation process.

Figure 3:
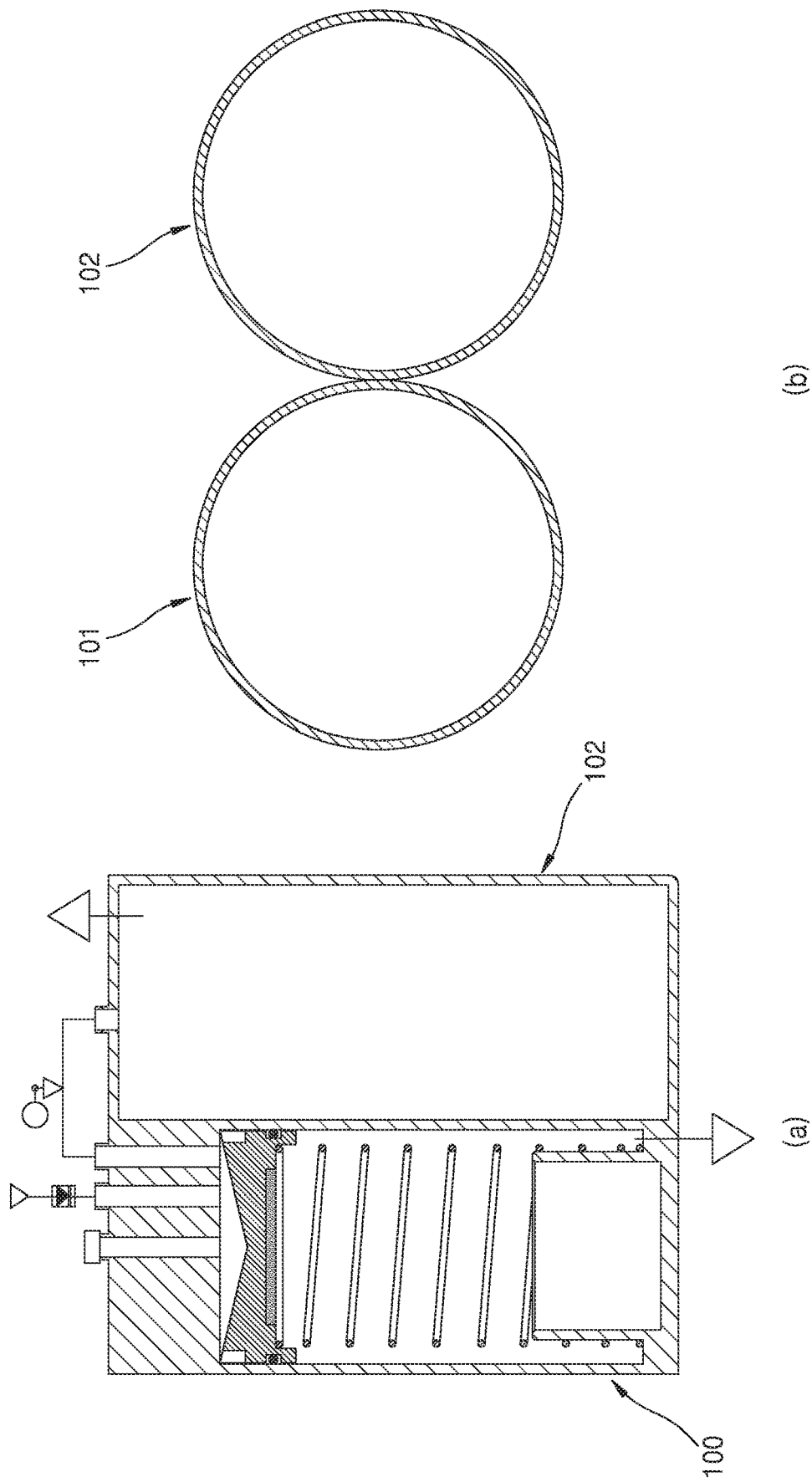

(a) and (b) of FIG. 3 show a longitudinal cross-section and a traverse cross-section of a modified form of the centrifugal separation container according to the first embodiment of the present disclosure.

Figure 4:
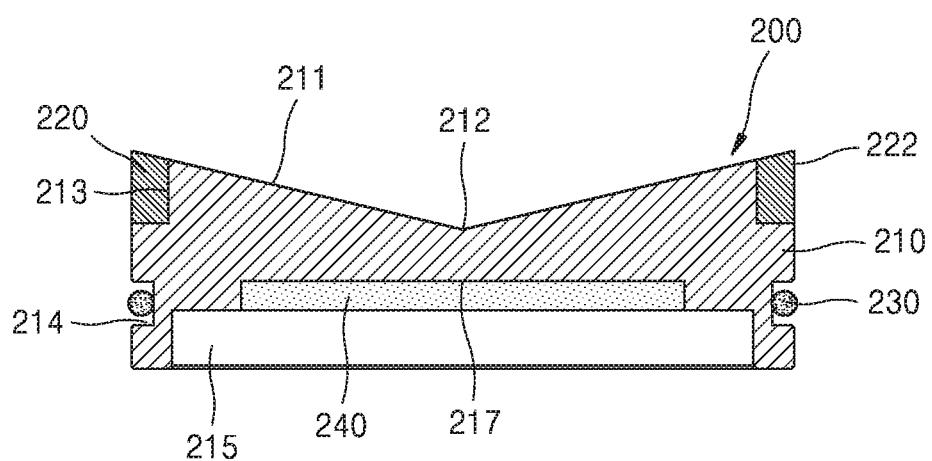
Figure 4:
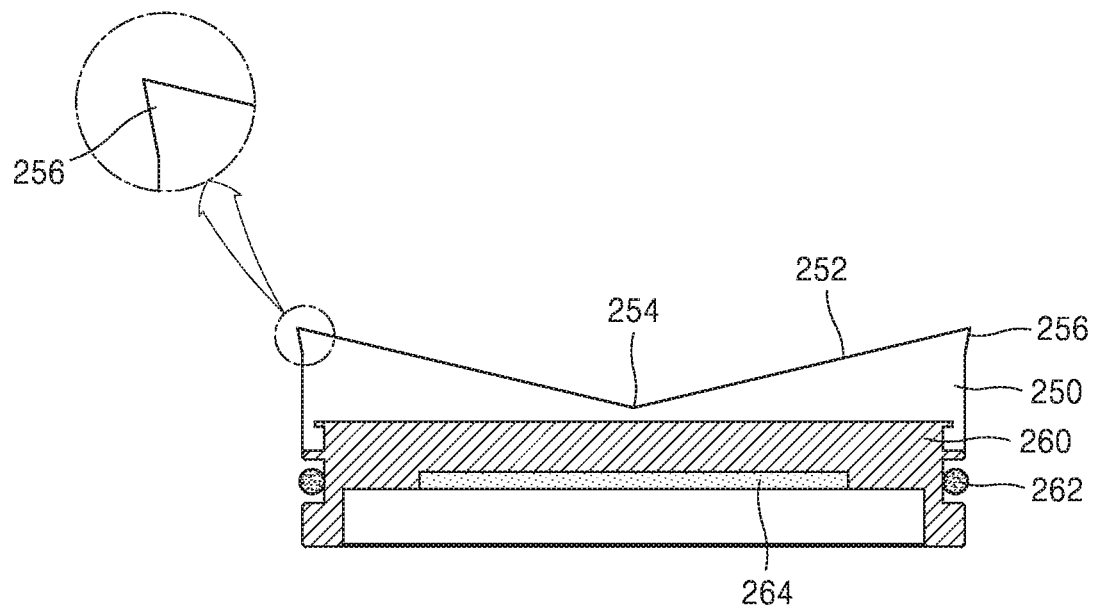

(a) and (b) of FIG. 4 show a first piston of a centrifugal separation container according to an embodiment of the present disclosure.

Figure 5A:
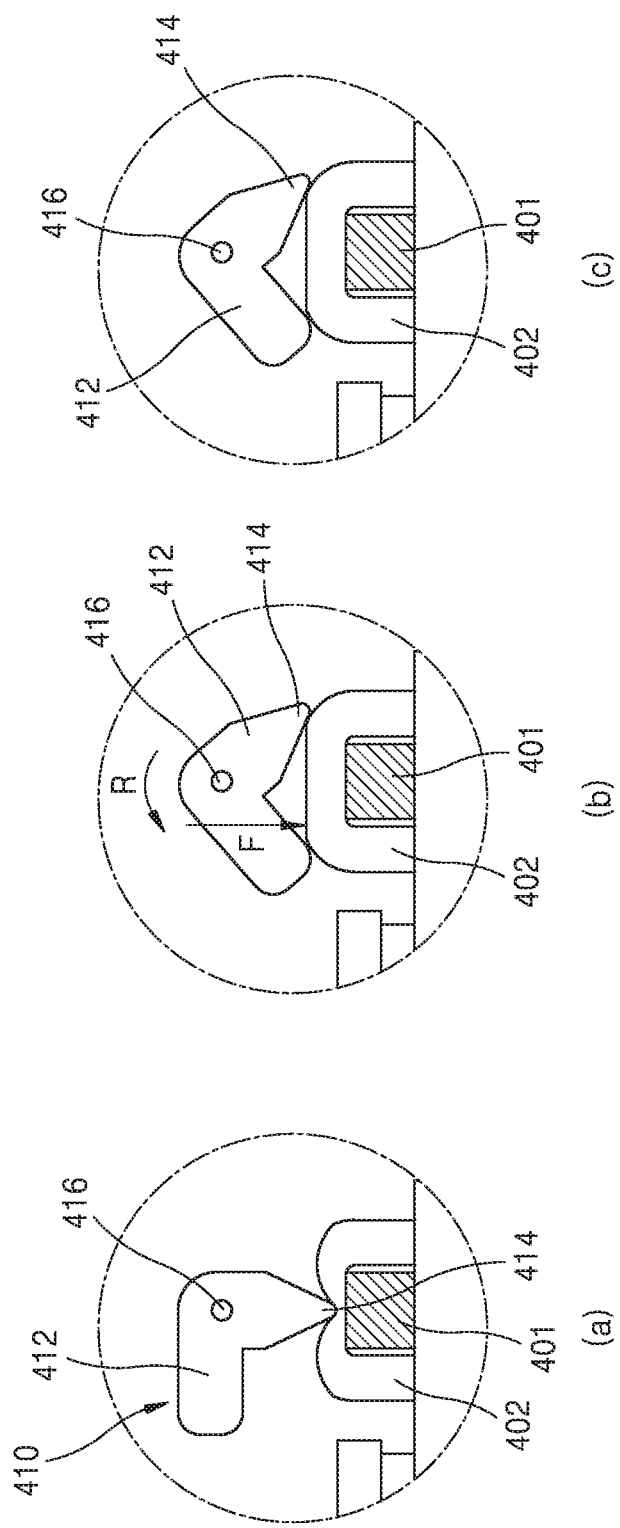
Figure 5B:
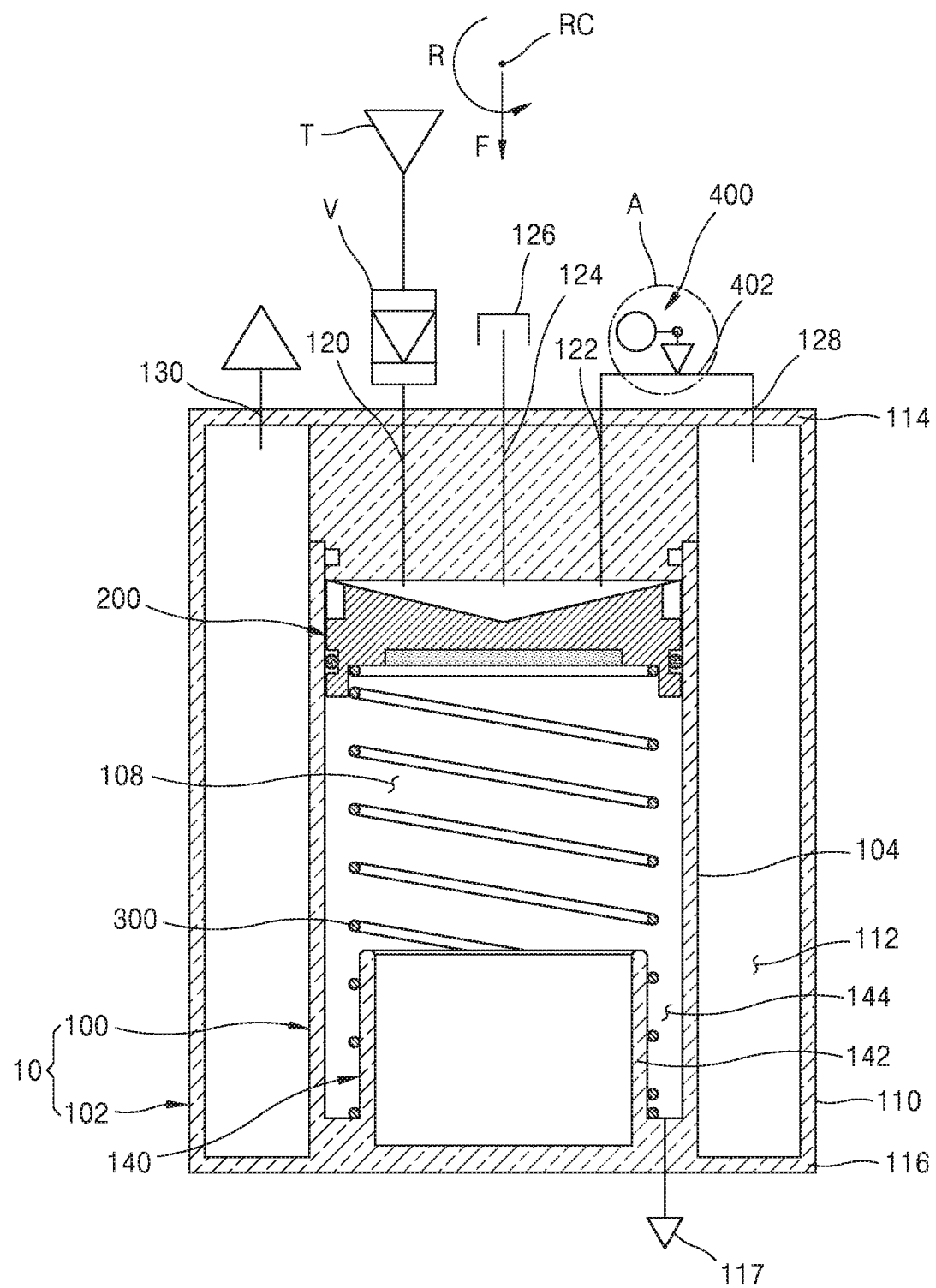

FIG. 5a shows a structure and operation of a first control valve of the centrifugal separation container according to the first embodiment of the present disclosure, and FIG. 5b shows a direction in which a centrifugal force is applied in the centrifugal separation container according to the first embodiment of the present disclosure.

Figure 6:
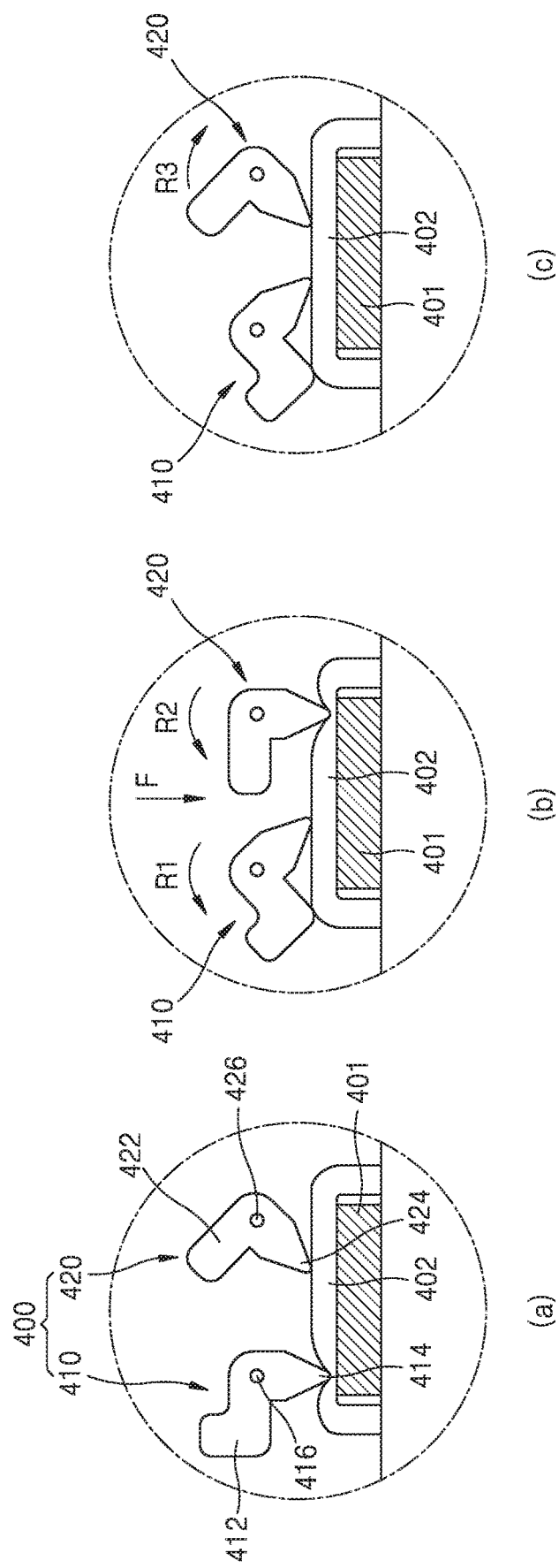

FIG. 6 shows a structure and operation of a first control valve of a centrifugal separation container according to a second embodiment of the present disclosure.

Figure 7:
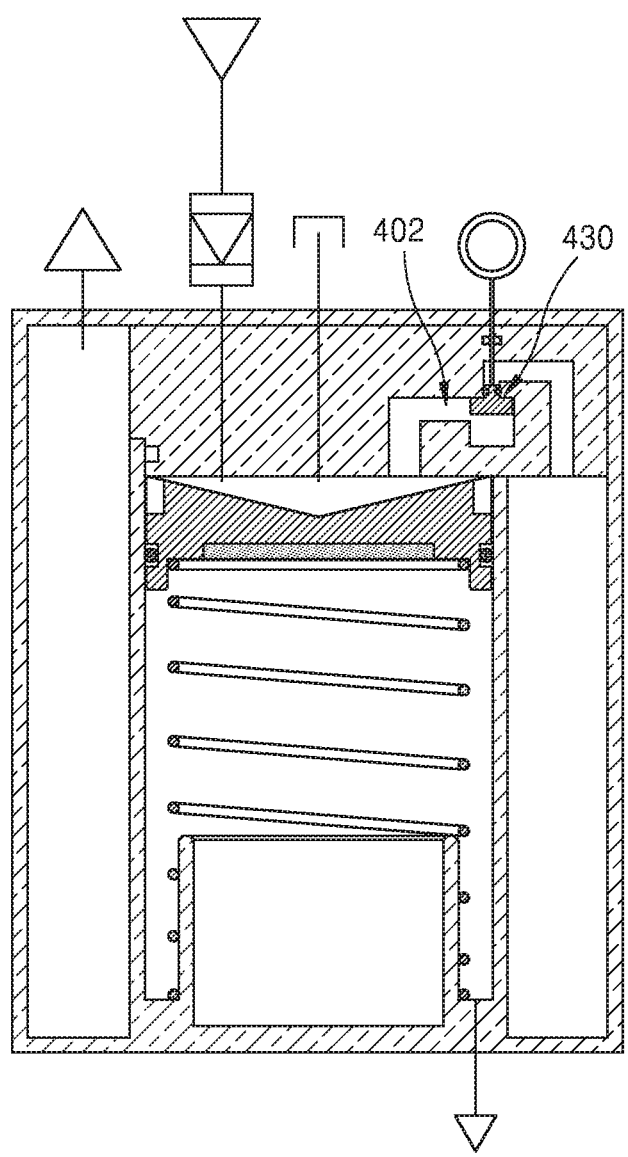

FIG. 7 shows a longitudinal cross-section of a centrifugal separation container according to a third embodiment of the present disclosure.

Figure 8A:
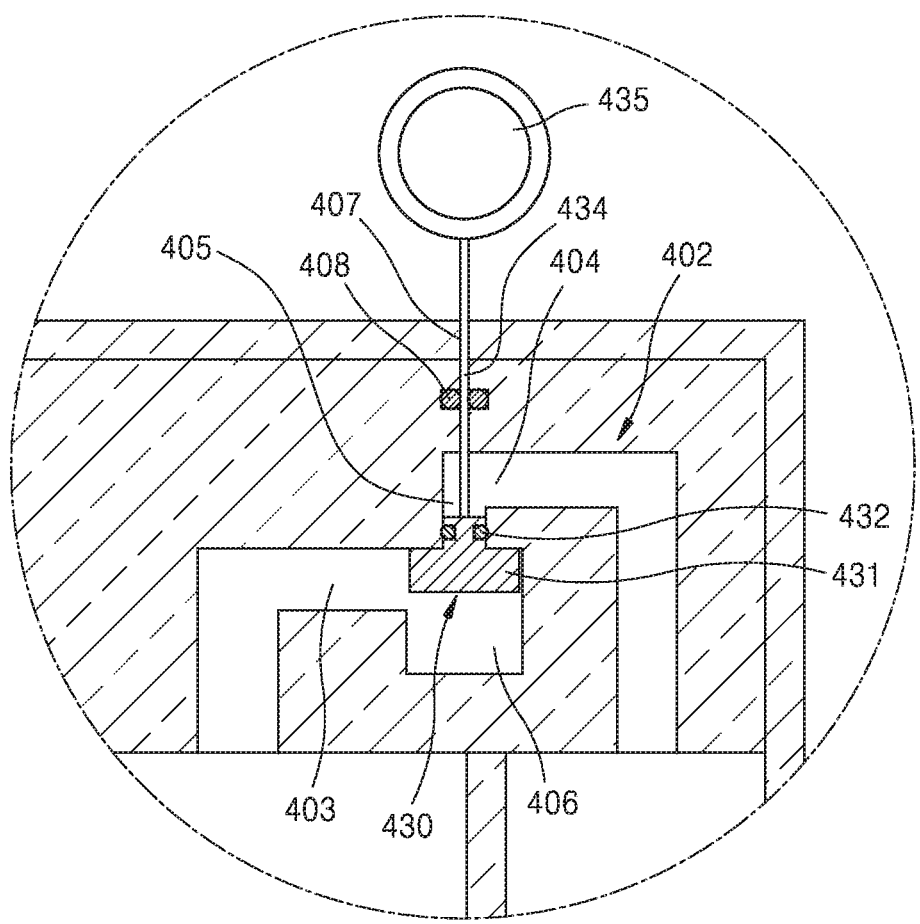
Figure 8B:
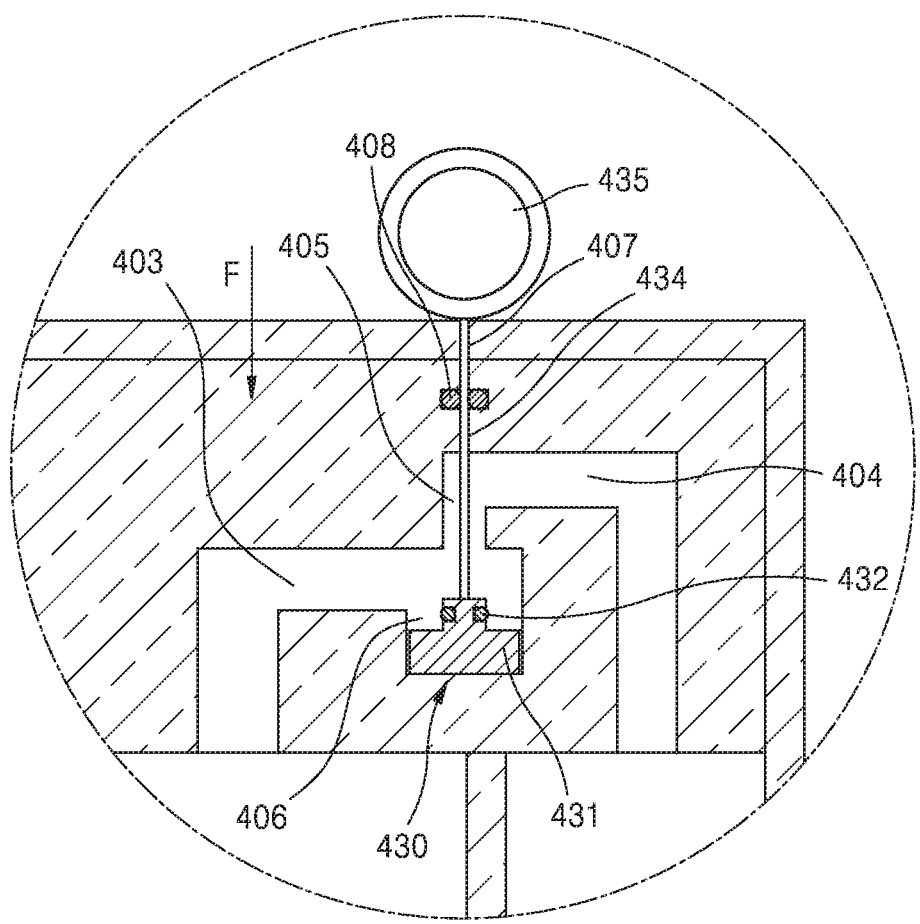

FIGS. 8a and 8b show a structure and operation of a first control valve of the centrifugal separation container according to the third embodiment of the present disclosure.

Figure 9A:
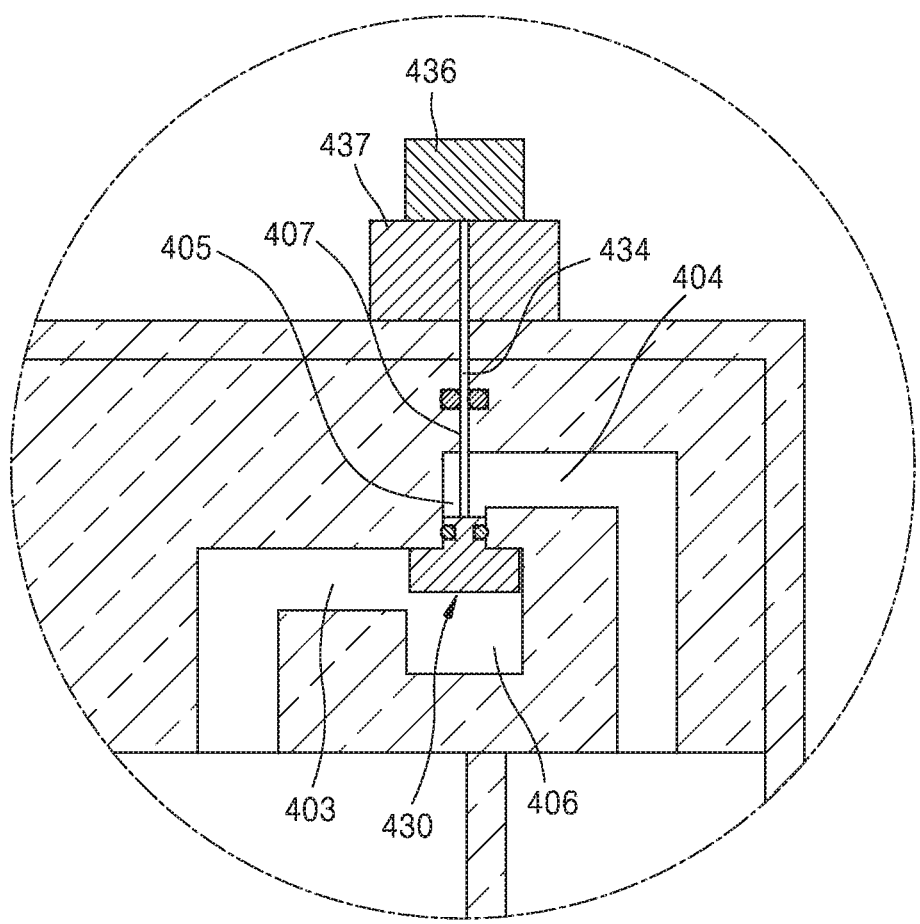
Figure 9B:
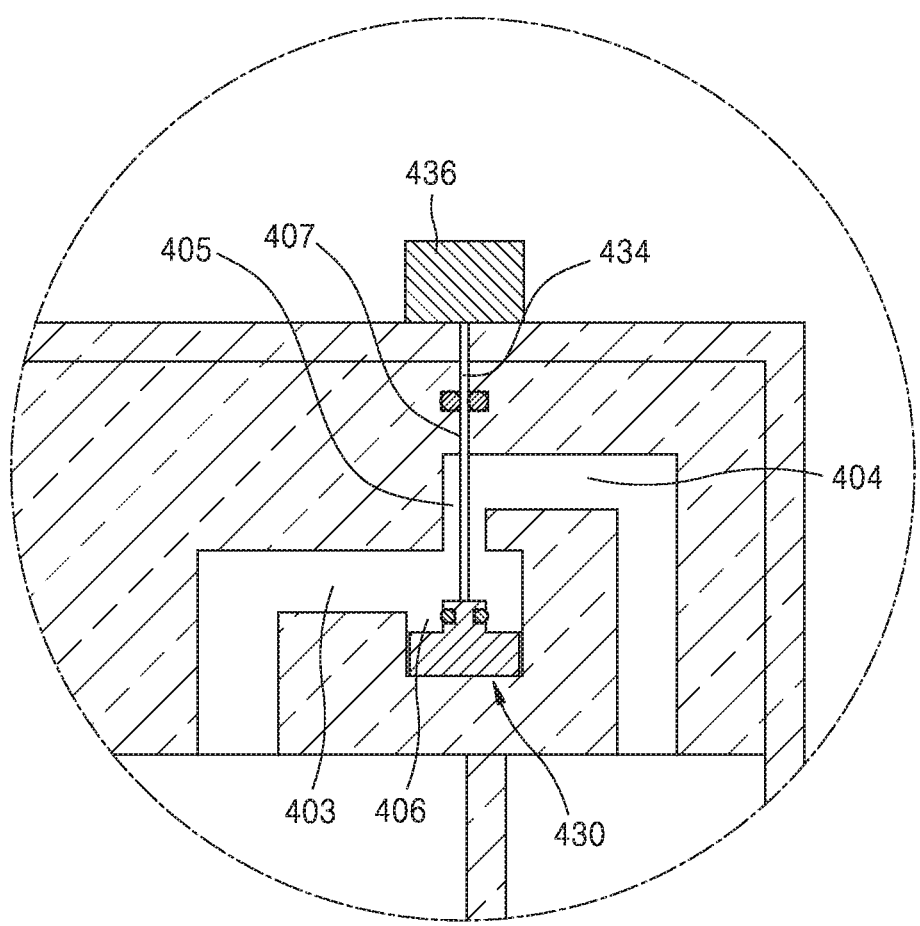
Figure 9C:
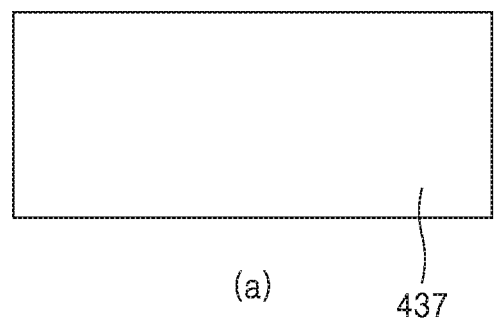
Figure 9C:
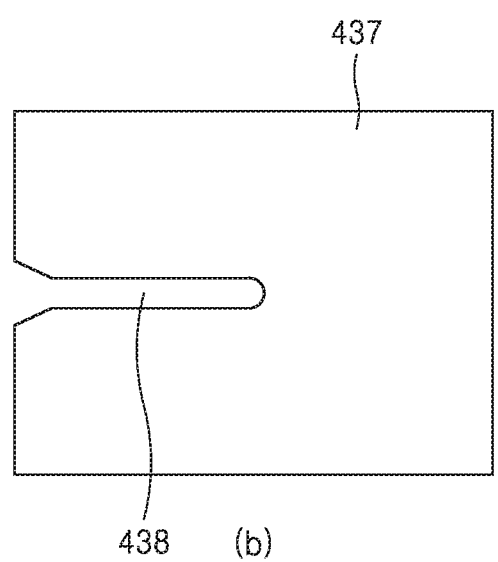

FIGS. 9a and 9b show a modified example of the first control valve according to the third embodiment of the present disclosure and an operation of the modified example, and (a) and (b) of FIG. 9c show the shape of a stopper, seen in different directions.

Figure 10:
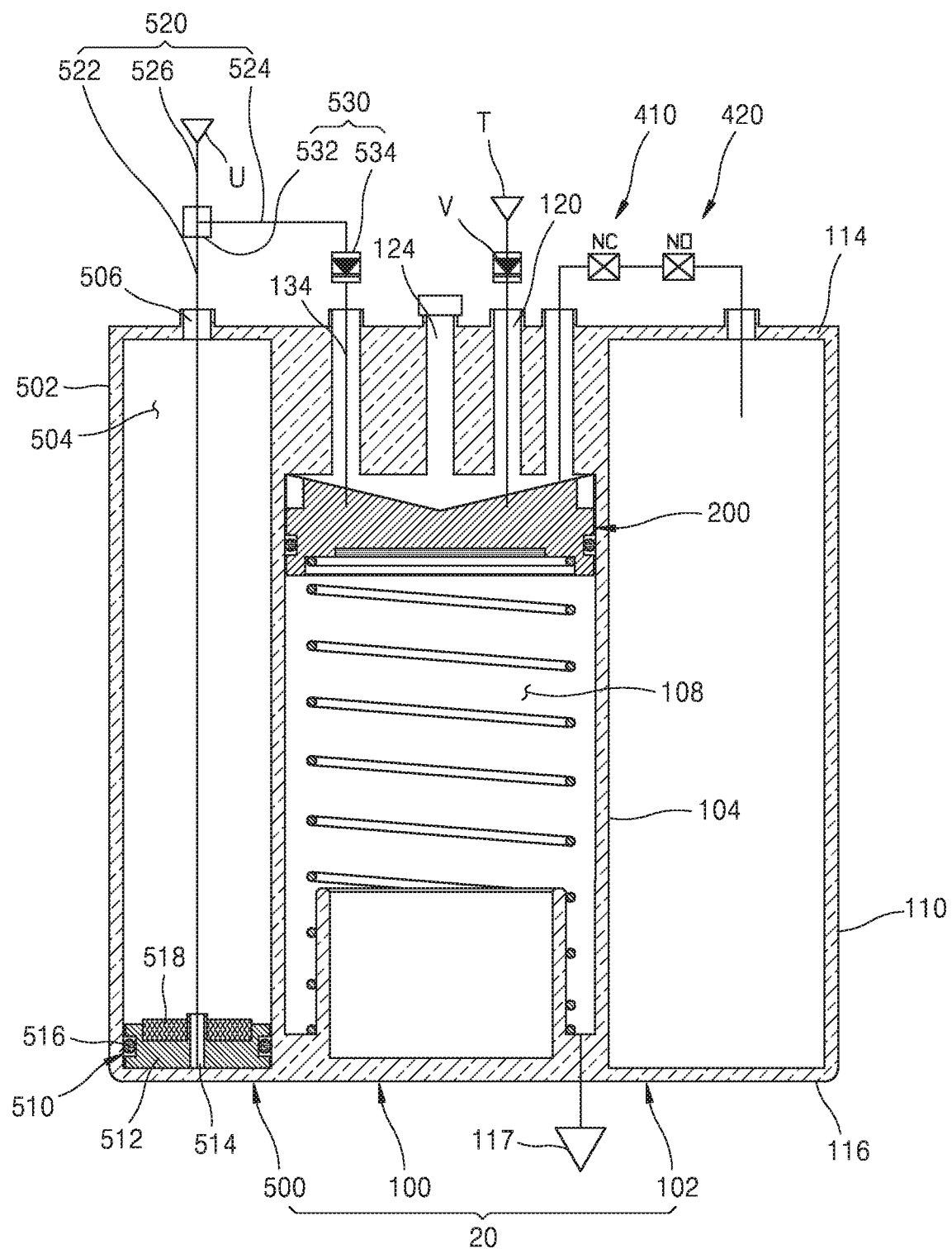

FIG. 10 shows a longitudinal cross-section of a centrifugal separation container according to a fourth embodiment of the present disclosure.

Figure 11:
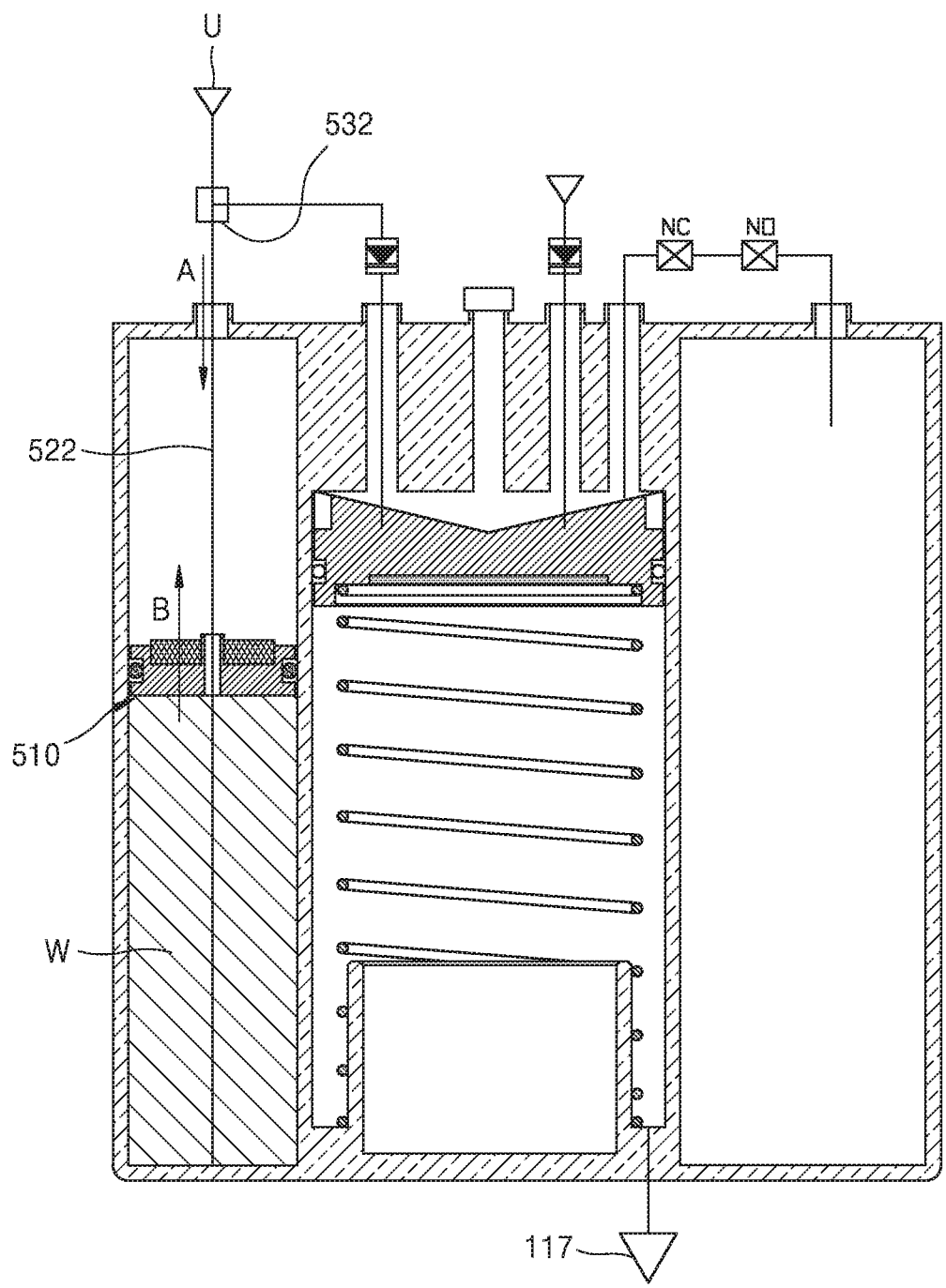
Figure 12:
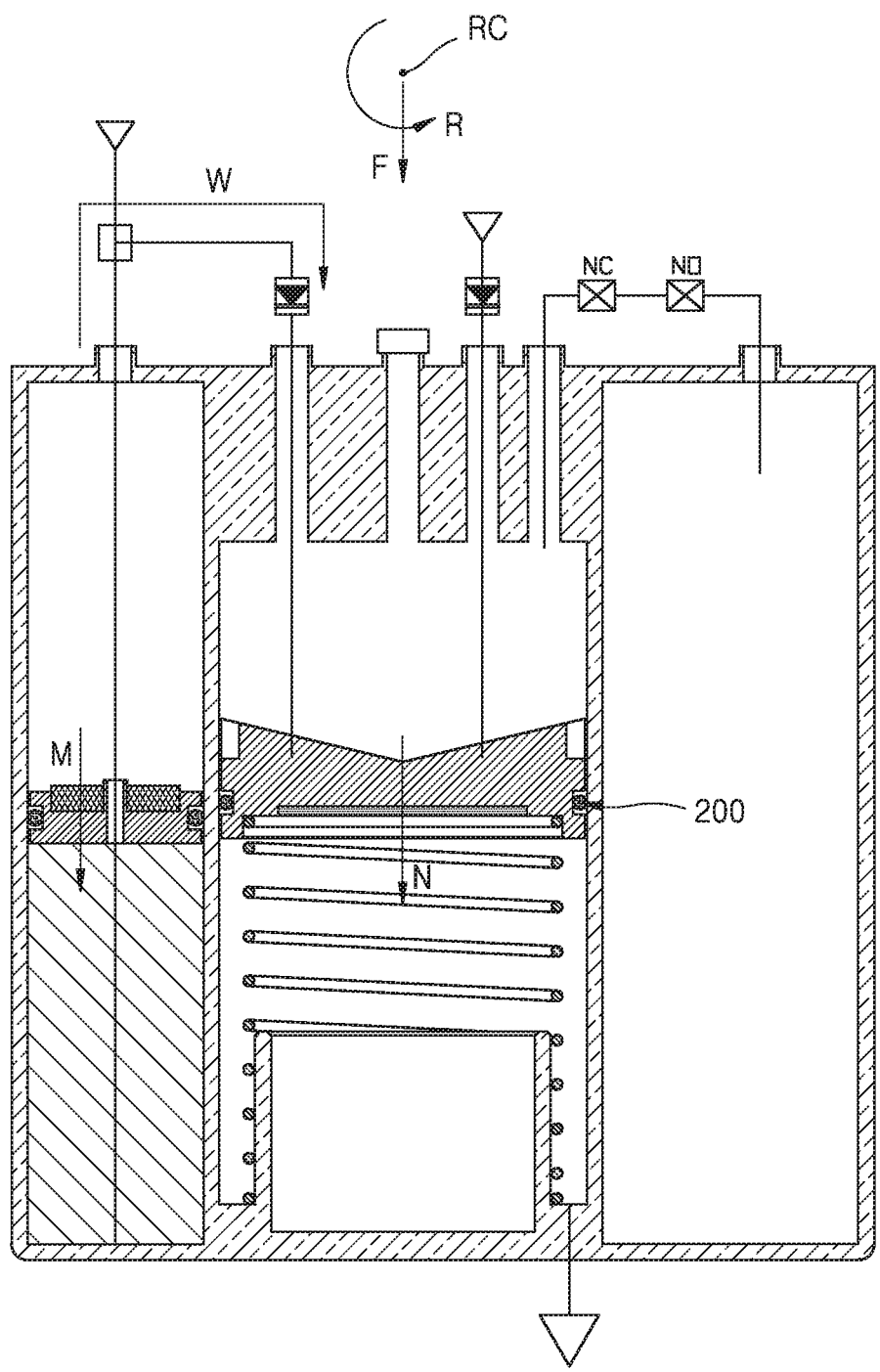

FIGS. 11 and 12 show a movement process of a movement target material in a third container of the centrifugal separation container according to the fourth embodiment of the present disclosure.

Figure 13A:
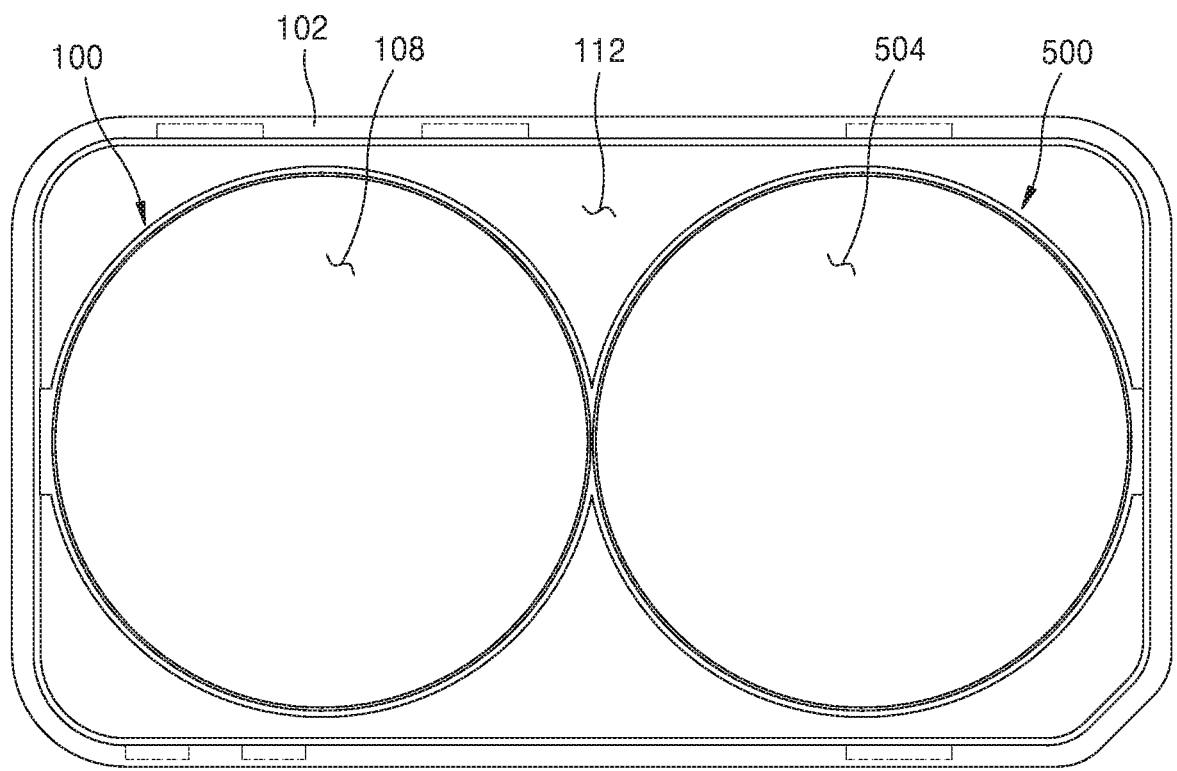
Figure 13B:
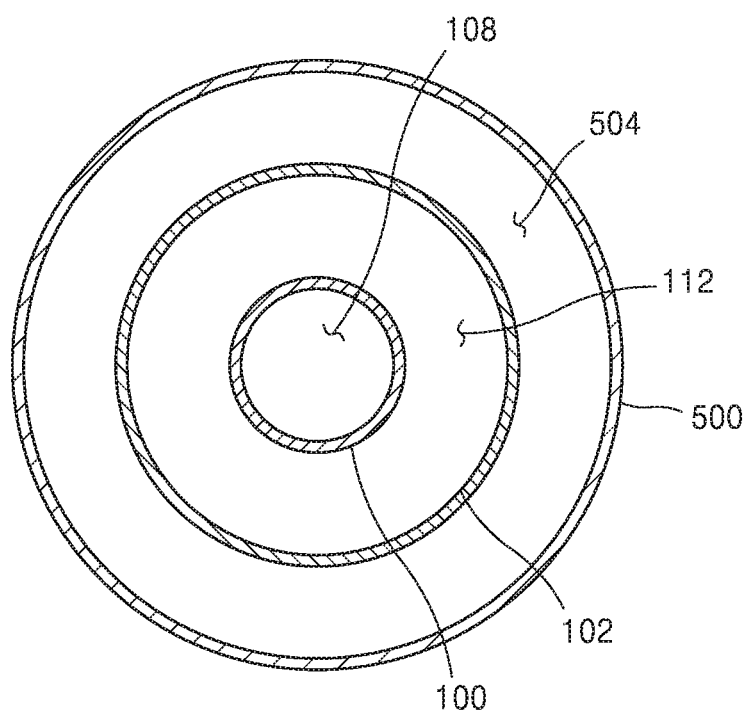
Figure 13C:
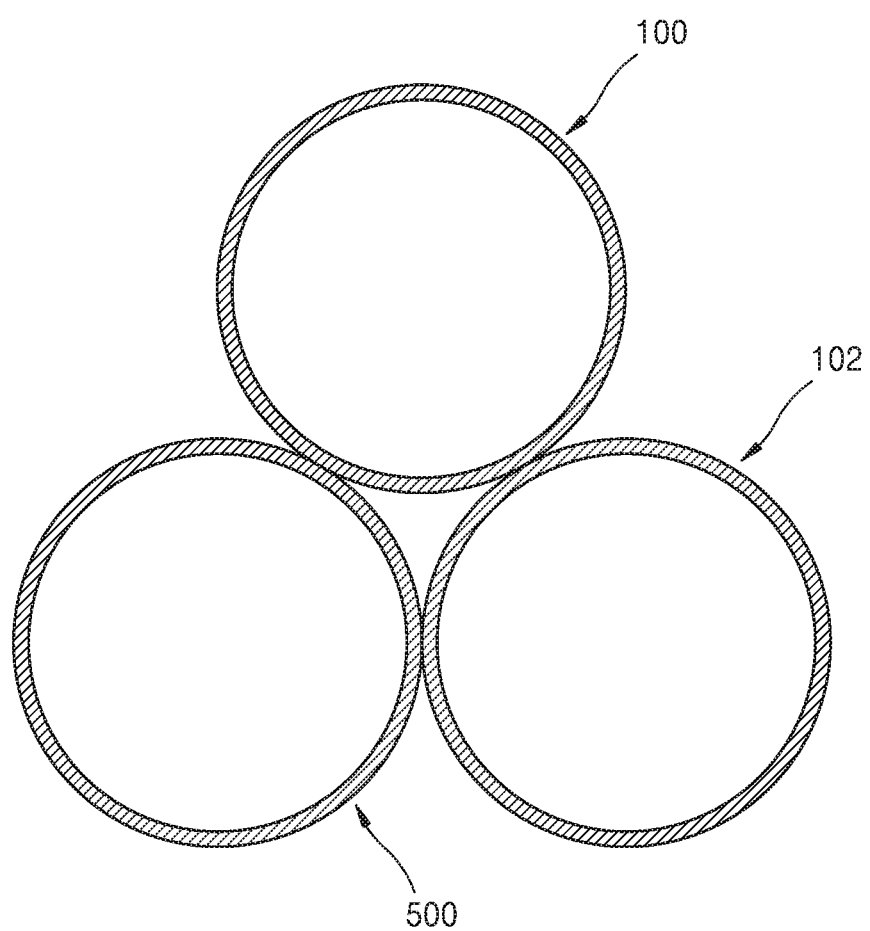

FIGS. 13a to 13c show traverse cross-sections of modified forms of the centrifugal separation container according to the fourth embodiment of the present disclosure.

Figure 14A:
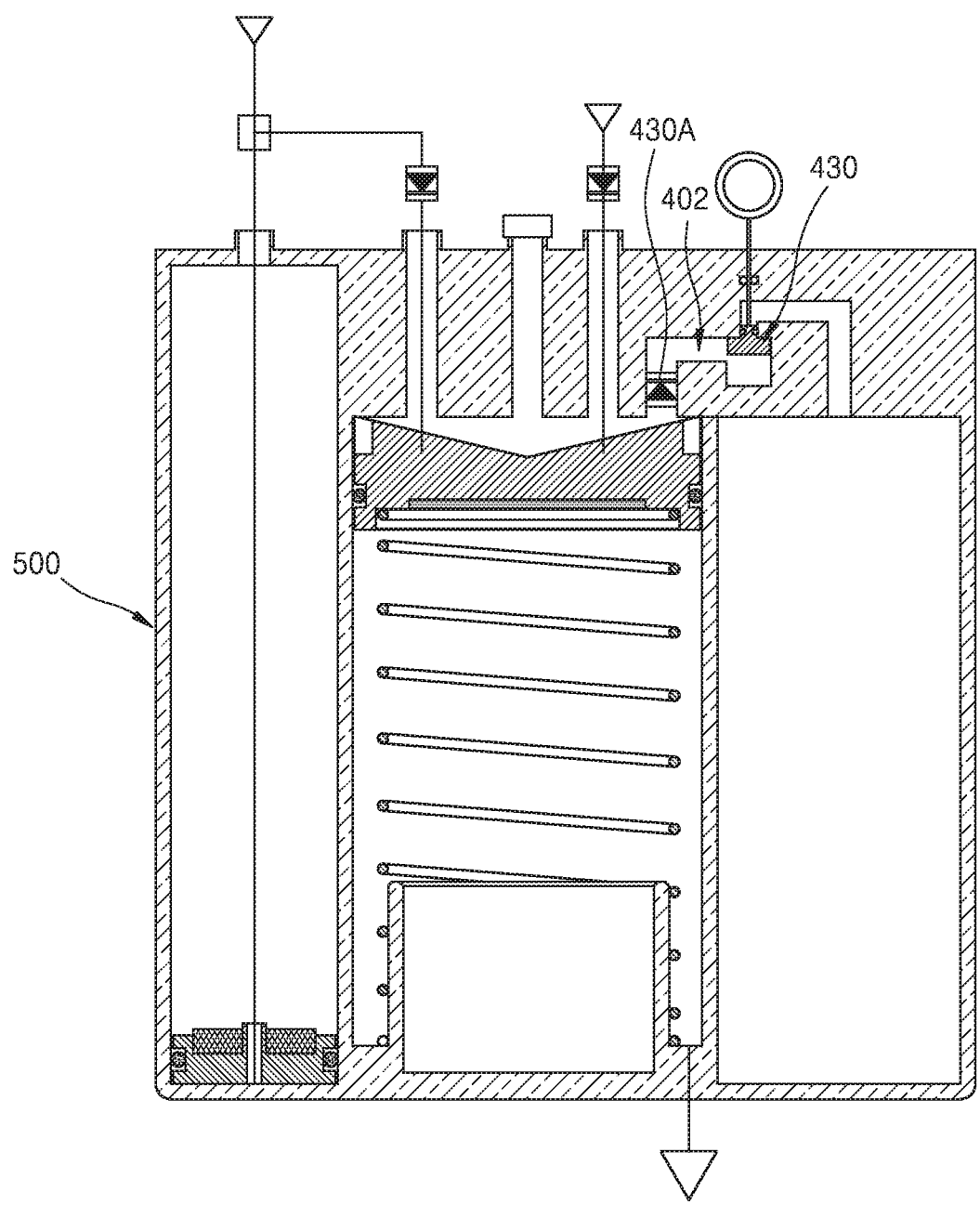
Figure 14B:
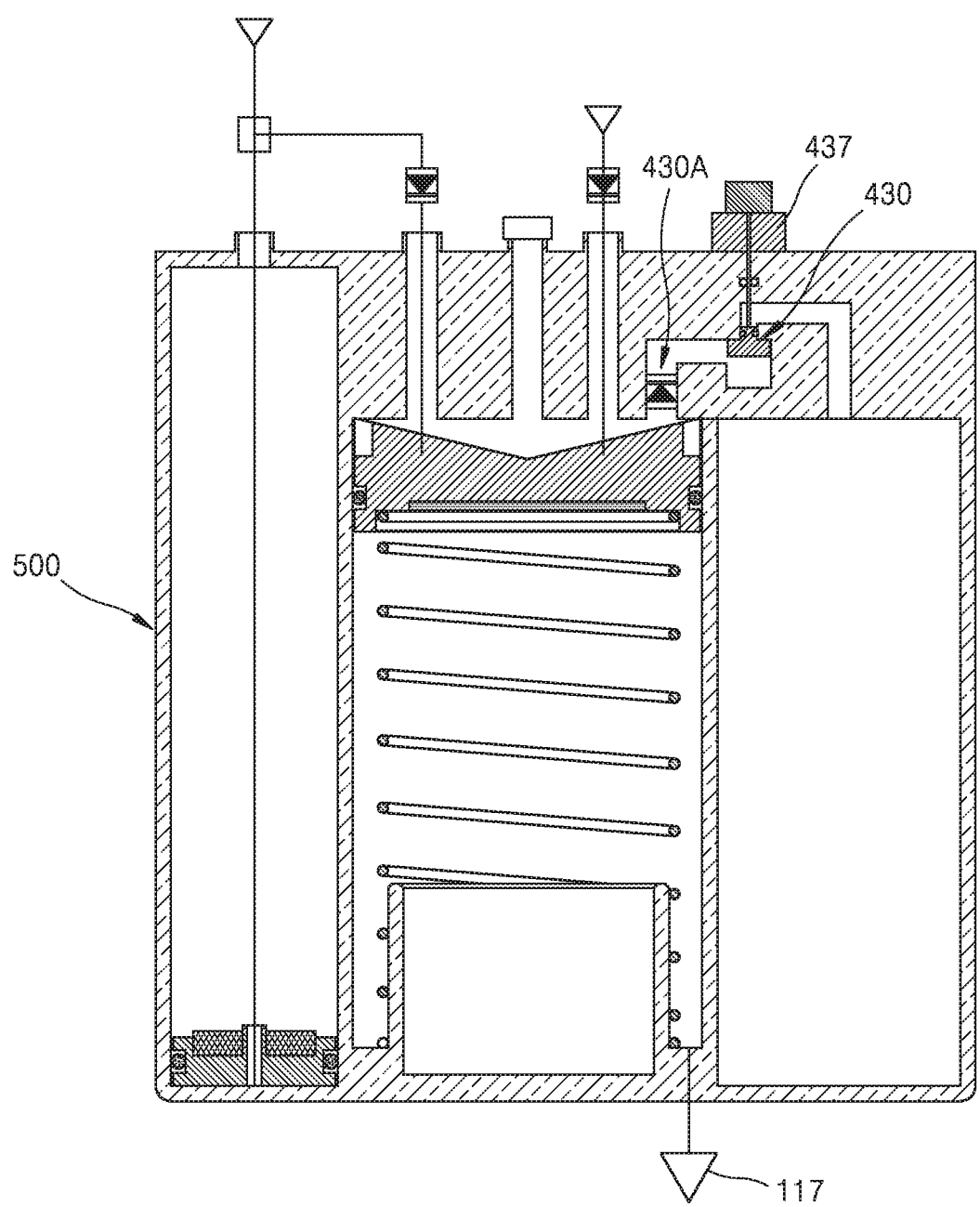

FIGS. 14a and 14b show longitudinal cross-sections of other modified forms of the centrifugal separation container according to the fourth embodiment of the present disclosure.

Figure 15:
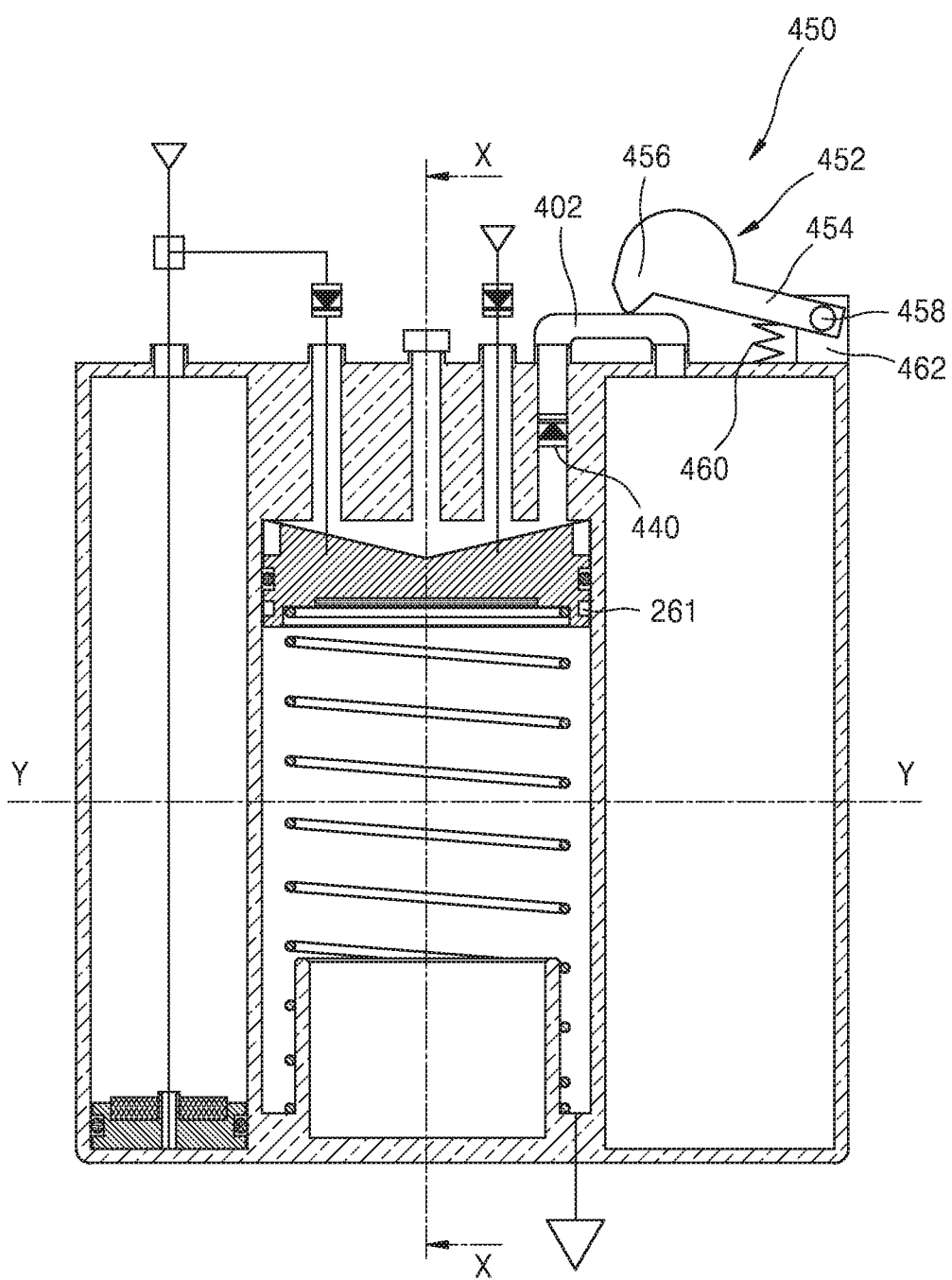

FIG. 15 shows a longitudinal cross-section of a centrifugal separation container according to a fifth embodiment of the present disclosure.

Figure 16:
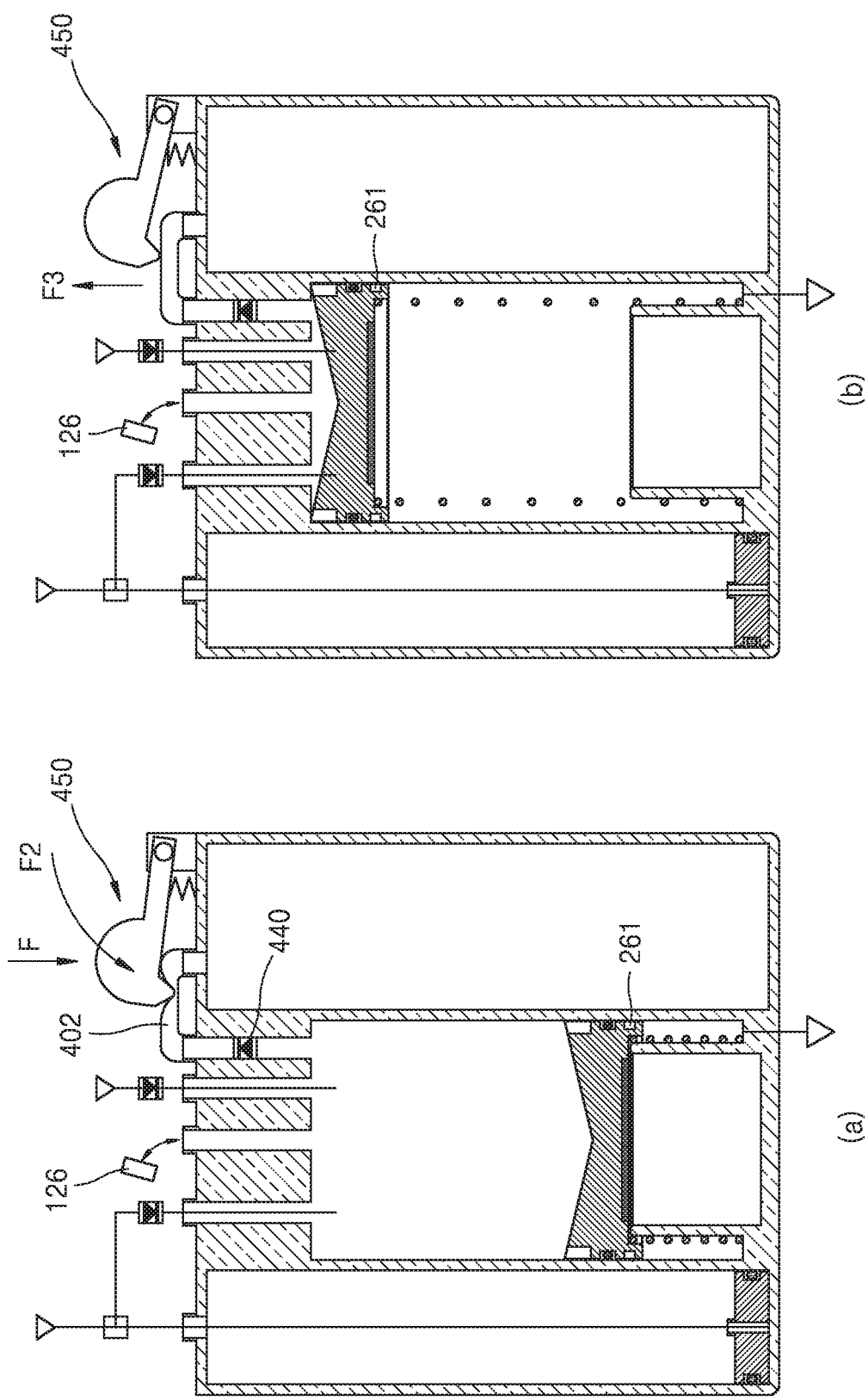

(a) and (b) of FIG. 16 show an operation of the centrifugal separation container according to the fifth embodiment of the present disclosure.

Figure 17:
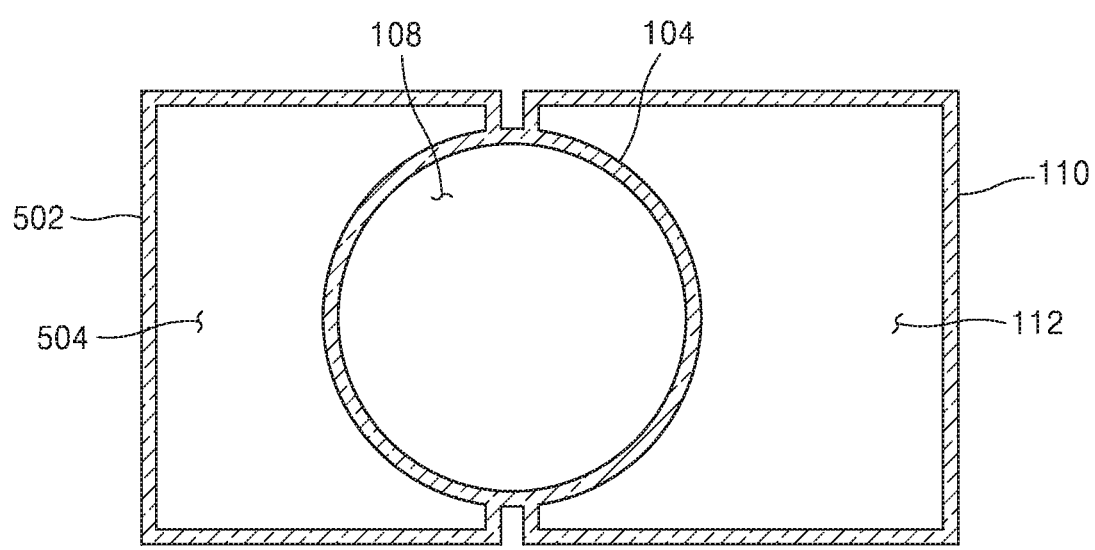

FIG. 17 shows a cross-section taken along line Y-Y of FIG. 15.

Figure 18:
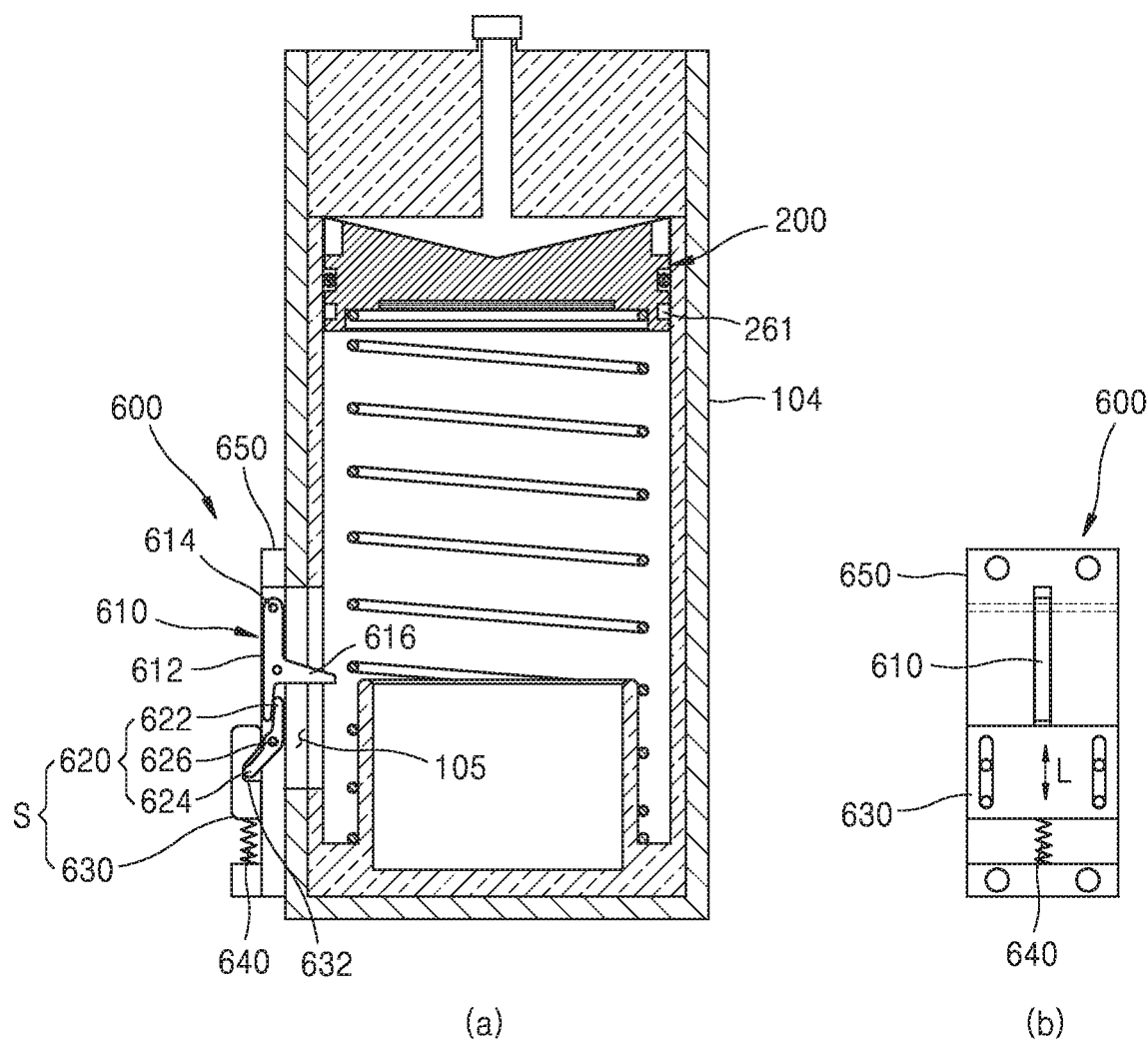

FIG. 18 shows a cross-section taken along line X-X of FIG. 15.

Figure 19:
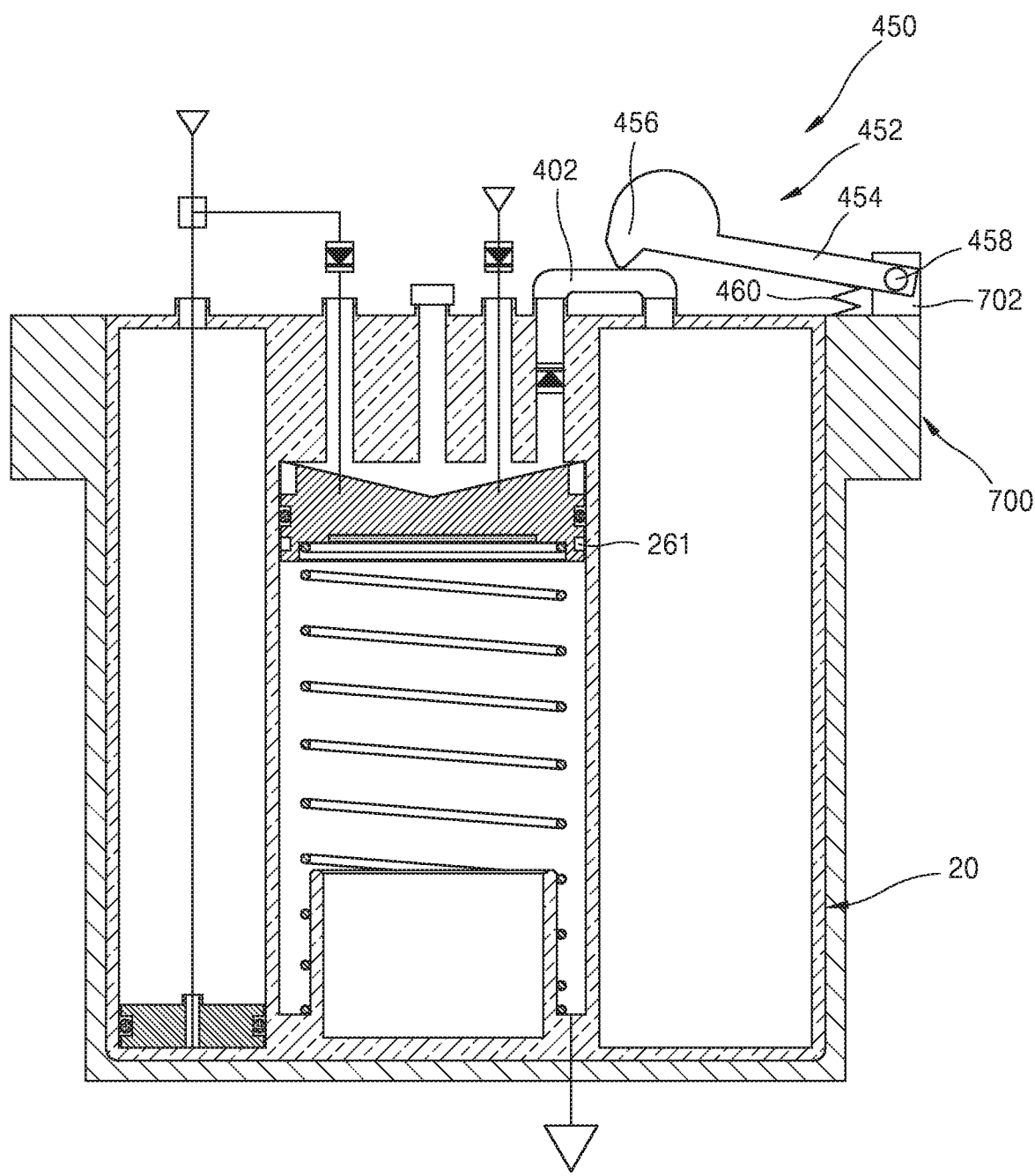

FIG. 19 shows a longitudinal cross-section of a centrifugal separation container according to a sixth embodiment of the present disclosure.

Figure 20:
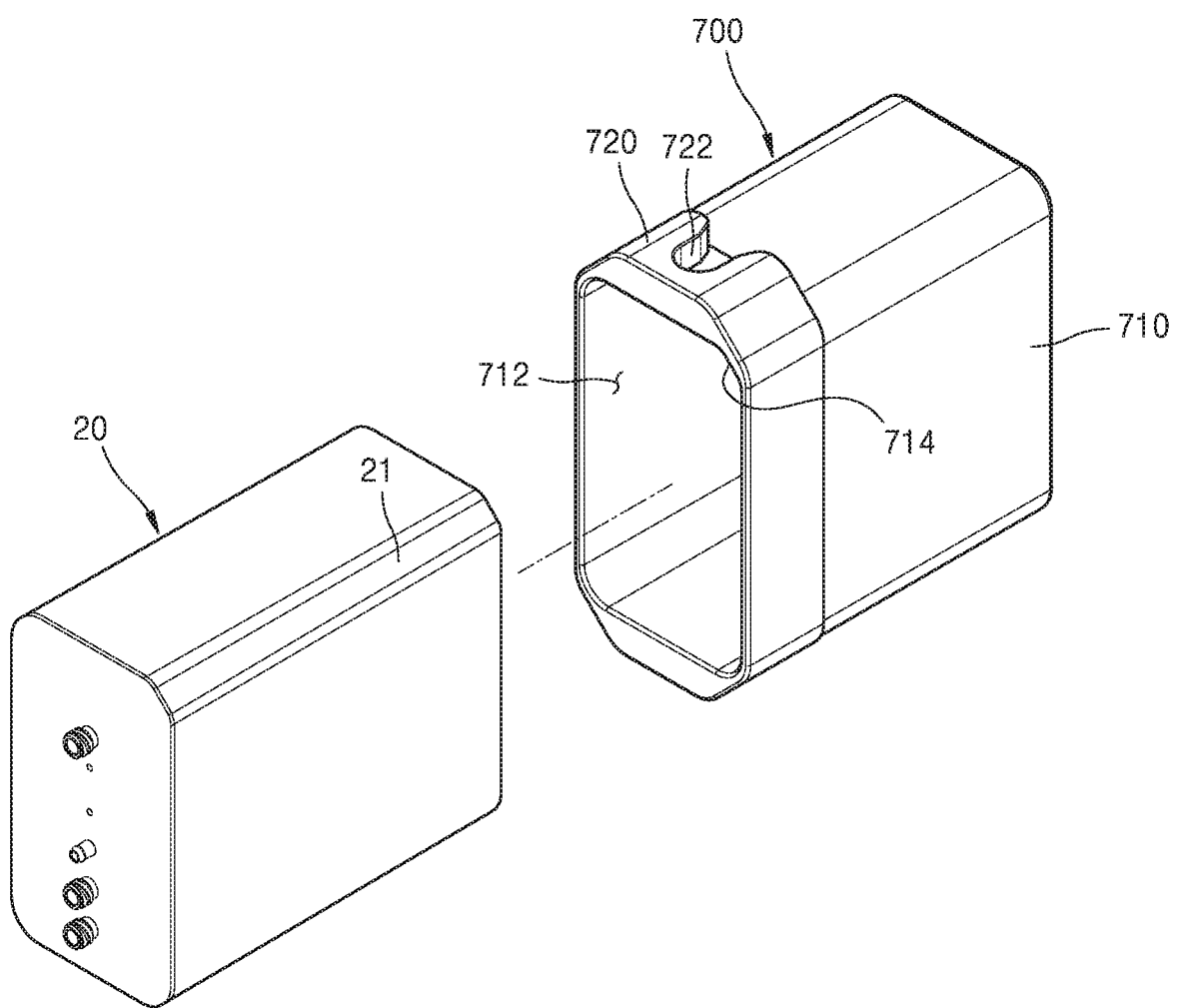

FIG. 20 shows a coupling structure of a bucket and a centrifugal separation container according to an embodiment of the present disclosure.

Figure 21:
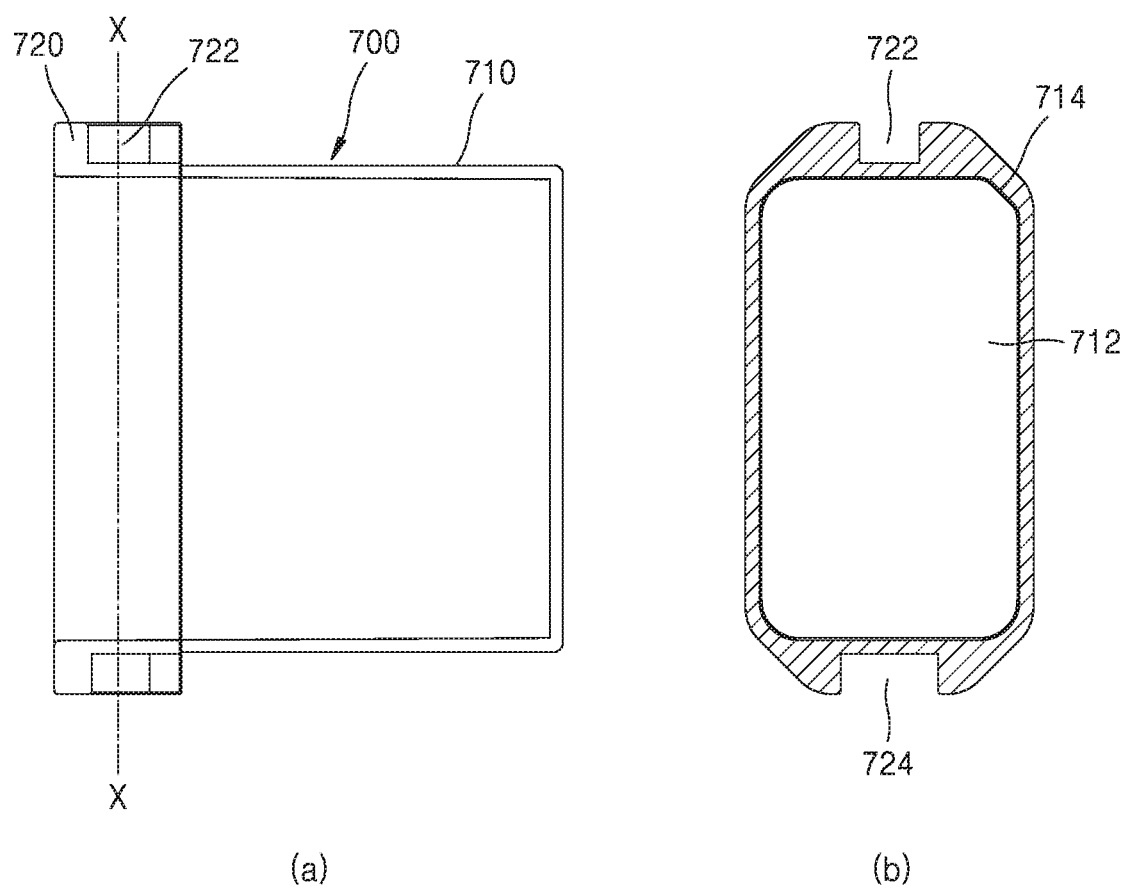

(a) of FIG. 21 shows a longitudinal cross-section of a bucket coupled with a centrifugal separation container according to an embodiment of the present disclosure, and (b) of FIG. 21 shows a cross-section taken along line X-X of (a) of FIG. 21.

Figure 22:
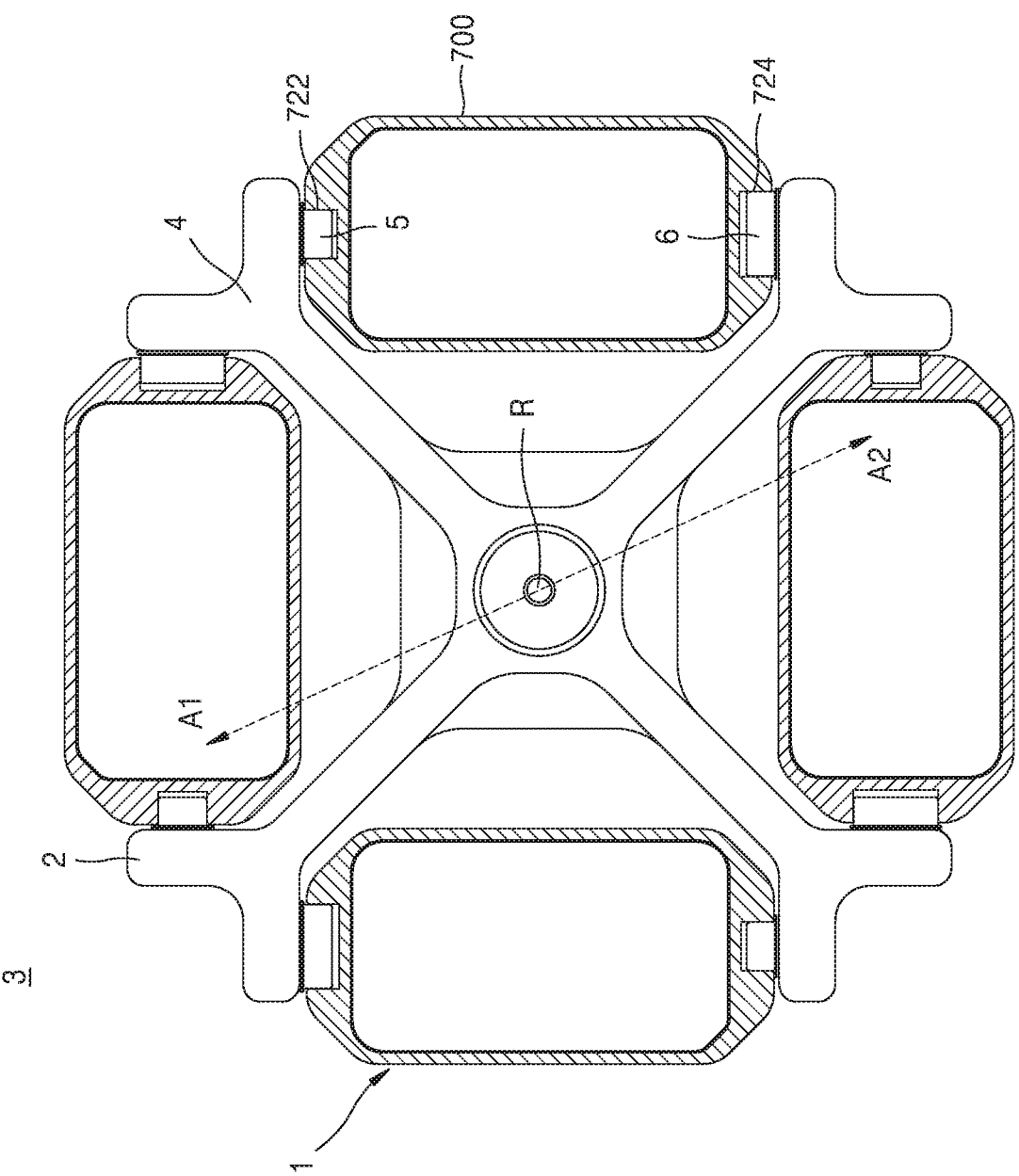

FIG. 22 shows a coupling structure of a centrifugal separation container according to an embodiment of the present disclosure, configured by coupling a bucket with a rotation body.

Figure 23:
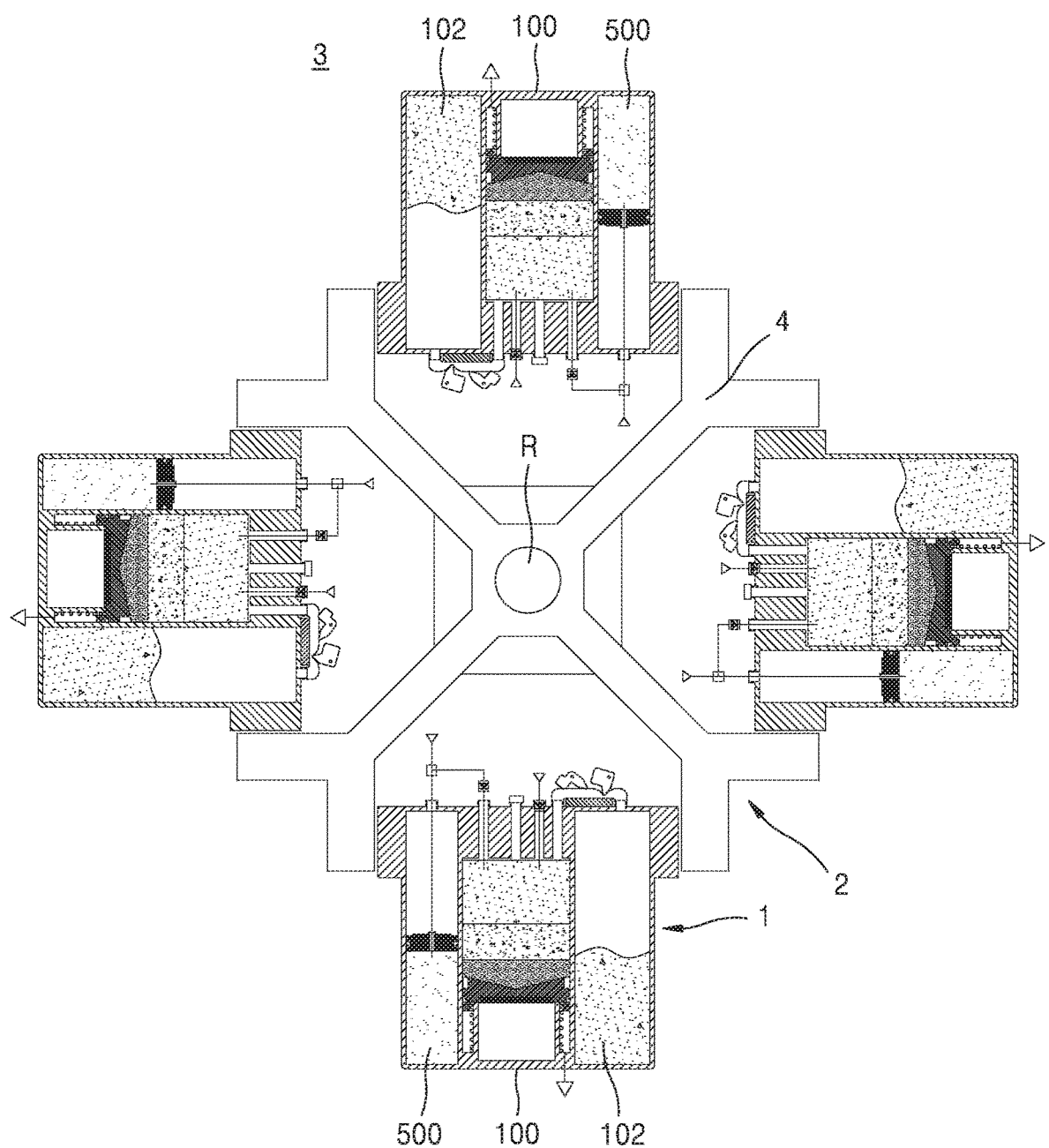

FIG. 23 shows a coupling structure of a centrifugal separation container according to an embodiment of the present disclosure, configured by coupling a bucket in which the centrifugal separation container is installed with a rotation body.

FIGS. 24 to 27 show an operation process of a coupling structure of a centrifugal separation container according to an embodiment of the present disclosure.

BEST MODE

A centrifugal separation container according to an embodiment of the present disclosure for separating a material from tissue and body fluids using a centrifugal force, may include: a first container; a second container; a first piston positioned in the inside of the first container and configured to be movable up and down in the inside of the first container; an elastic body positioned below the first piston in the inside of the first container and configured to elastically bias the first piston upward; a first connecting duct having one end connected to the first container and the other end connected to the second container; and a first control valve operating by a centrifugal force and configured to open and close the first connecting duct.

MODE OF DISCLOSURE

Hereinafter, preferred embodiments of the present disclosure will be described with reference to the accompanying drawings.

Figure 1:
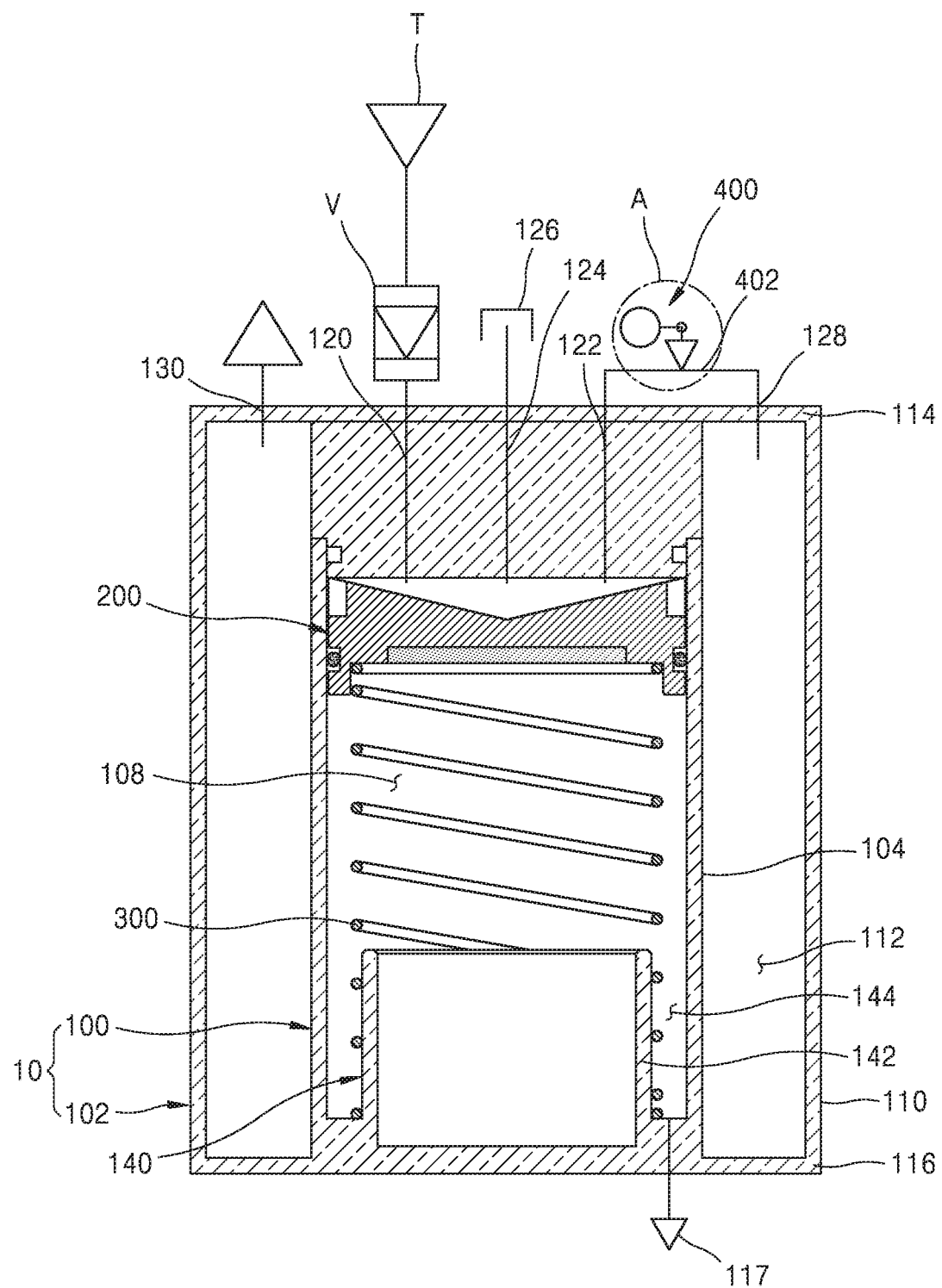
FIG. 1 shows a longitudinal cross-section of a centrifugal separation container according to a first embodiment of the present disclosure.
Figure 2:
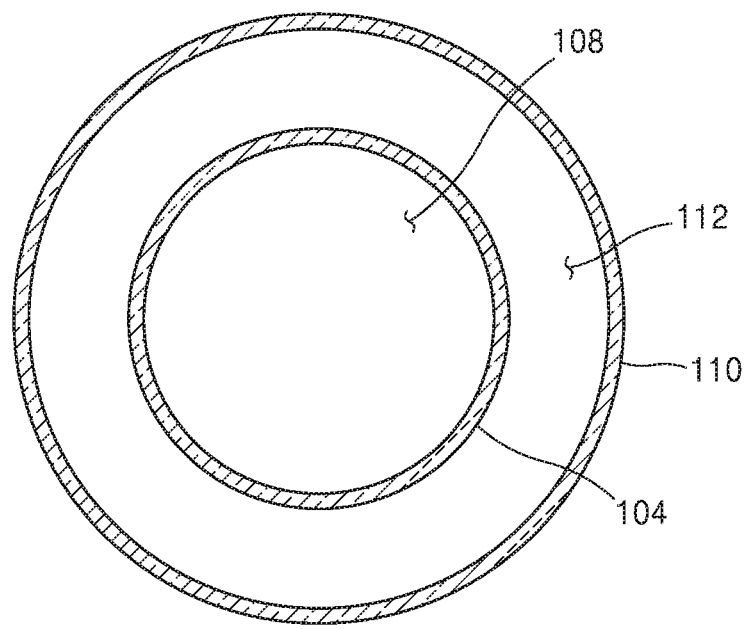
FIG. 2 shows a traverse cross-section of the centrifugal separation container shown in FIG. 1.

FIG. 1 shows a longitudinal cross-section of a centrifugal separation container according to a first embodiment of the present disclosure, FIG. 2 shows a traverse cross-section of the centrifugal separation container shown in FIG. 1, and (a) and (b) of FIG. 3 show a longitudinal cross-section and a traverse cross-section of a modified form of the centrifugal separation container according to the first embodiment of the present disclosure.

A centrifugal separation container according to a first embodiment of the present disclosure may include a first container 100, a second container 102, a first piston 200, an elastic body 300, a first connecting duct 402, and a first control valve 400.

The first container 100 may be a member in which a first space 108 is formed. For example, the first container 100 may be a member in which tissue and body fluids are injected to be centrifugally separated. That is, the first container 100 may be a predetermined container for separation. The second container 102 may be a member in which a second space 112 is formed. For example, the second container 102 may be a member in which a material separated and discharged from the first container 100 is accommodated. That is, the second container 102 may be a predetermined container for discharging. As shown in FIG. 1, the first container 100 may be coupled with the second container 102 to construct a double container 10. However, the first container 100 and the second container 102 may be configured as separated members, or arranged side-by-side as shown in FIG. 3.

The double container 10 may have a structure including the first container 100 and the second container 102. The double container 10 may include a first side portion 104 having a cavity, a second side portion 110 disposed around the first side portion 104 and having a cavity, and a top portion 110 and a bottom portion 116 respectively coupled with upper and lower ends of the first side portion 104 and the second side portion 110, wherein the first space 108 is formed in the inside of the first side portion 104 and the second space 112 is formed between the second side portion 110 and the first side portion 104.

The first side portion 104 may be in the shape of a standing cylinder and have a pipe shape with an inside cavity extending vertically. The upper and lower ends of the first side portion 104 may be coupled with the top portion 114 and the bottom portion 116, respectively. Accordingly, the inside cavity of the first side portion 104 may form the first space 108 of the first container 100.

The second side portion 110 may surround an outer side of the first side portion 104 and be spaced a predetermined distance from the first side portion 104 to form the second space 112 together with the first side portion 104. Accordingly, as seen from the traverse cross-section of the centrifugal separation container according to the current embodiment, as shown in FIG. 2, the first side portion 104 of the first container 100 and the second side portion 110 of the second container 102 may have a concentric double pipe structure. However, the first container 100 and the second container 102 may be arranged side-by-side.

The top portion 114 may form a top surface of the double container 10 when the double container 10 stands as shown in FIG. 1. Preferably, according to an embodiment, the top portion 114 may be configured to be detachably coupled with the first side portion 104 of the first container 100 and the second side portion 112.

The top portion 114 may include a first opening 120, a second opening 122, a third opening 124, a fourth opening 128, and a fifth opening 130.

Each of the first opening 120, the second opening 122, and the third opening 124 may be in the form of a passage vertically penetrating the top portion 114 above the first space 108.

The first opening 120 may form a passage functioning as an inlet through which tissue and body fluids are injected into the first space 108. Meanwhile, one end of the first opening 120 may be connected to a one-way valve V and injection means T. The second opening 122 may form a passage functioning as an outlet through which a predetermined discharge target material separated in the first space 108 is discharged from the first space 108 to the outside. Also, the third opening 124 may form a passage functioning as an extraction hole for extracting a material separated in the first space 108 to the outside. Also, the third opening 124 may include a third opening cap 126 for covering the third opening 124. The third opening cap 126 may be opened or closed when the centrifugal separation container according to the present disclosure is used.

Each of the fourth opening 128 and the fifth opening 130 may be formed in the shape of a passage vertically penetrating the top portion 114 above the second space 112. The fourth opening 128 may form a passage through which the discharge target material discharged from the second opening 122 is injected into the second space 112. The fifth opening 130 may form a passage through which the discharge target material in the second space 112 is discharged to the outside or air in the second space 112 is discharged to the outside.

Meanwhile, FIG. 1 shows a case in which the centrifugal separation container includes all of the first opening 120, the second opening 122, the third opening 124, the fourth opening 128, and the fifth opening 130. However, the present disclosure is not limited to this. For example, an embodiment in which at least two or three of the first opening 120, the second opening 122, and the third opening 124 are integrated into one so that injection, discharge, and extraction are selectively performed through one or two openings is also possible. The fourth opening 128 and the fifth opening 130 may also be integrated into one opening so as to function in the same manner.

The bottom portion 116 may form a bottom surface when the double container 10 stands as shown in FIG. 1. The bottom portion 116 may be coupled with the lower ends of the first side portion 104 and the second side portion 112.

According to an embodiment, the bottom portion 116 may also be detachably coupled with the first side portion 104 of the first container 100 and the second side portion 112, like the top portion 114.

Meanwhile, in the bottom portion 116, a predetermined air vent 117 may be formed. The air vent 117 may be formed in the bottom of the first space 108 of the first container 100, and when the first piston 200 which will be described below moves up and down, the air vent 117 may ventilate air below the first piston 200 to the outside and have a filter therein.

On the bottom portion 116, a piston stopper 140 may protrude upward.

The piston stopper 140 may be a member protruding to a predetermined height from the bottom portion 116 of the first container 100. The piston stopper 140 may be disposed in the first container 100, that is, in the first space 108 to be positioned below the first piston 200 as described later.

More specifically, the piston stopper 140 may be a structure standing with a predetermined height from the bottom portion 116 of the first container 100. For example, as shown in FIG. 1, the piston stopper 140 may be in the shape of a cylinder which has a side wall and whose top opens. Preferably, the first side portion 104 may be spaced a predetermined distance from the side wall 142 of the piston stopper 140 in a diameter direction with respect to the center of the first container 100. Accordingly, the first side portion 104 of the first container 100 and the side wall 142 of the piston stopper 140 may be concentrically arranged with a predetermined interval, and a ring-shaped recessed space 144 may be formed between the first side portion 104 and the side wall 142.

The piston stopper 140 may limit a position of the first piston 200 as described later to thus appropriately maintain a space above the first piston 200 of the first container 100. That is, when a predetermined material is injected into the space above the first piston 200 so that the first piston 200 falls down or when the first piston 200 receives a centrifugal force to fall down, the first piston 200 may stop on the piston stopper 140. Accordingly, the piston stopper 140 may accurately maintain a volume of the space above the first piston 200. Also, an effect according to the following description related to the elastic body 300 may be obtained.

According to the current embodiment, since the first container 100 is coupled with the second container 102 to form the double container 10, the centrifugal separation container of a more advantageous and compact structure and a centrifugal separator having the centrifugal separation container may be provided.

In addition to the above-described embodiment, an embodiment shown in FIG. 3 is also possible. The embodiment of FIG. 3 may be the same as the above-described embodiment, except that the first container 100 and the second container 102 are positioned side-by-side so that the first space 108 and the second space 112 are positioned side-by-side.

Hereinafter, the first piston 200 will be described.

(a) and (b) of FIG. 4 show embodiments of the first piston 200 of the centrifugal separation container according to an embodiment of the present disclosure.

The first piston 200 may be positioned in the inside of the first container 100 and configured to be movable up and down. That is, the first piston 200 may move up and down between the bottom portion 116 and the top portion 114 in the inside of the first space 108.

The first piston 200 may include a first piston body 210, an upper ring 220, a side ring 230, and a weight 240.

The first piston body 210 may form a main body of the first piston 200. An upper surface of the first piston body 210 may face the top portion 114 of the first container 100, and a lower surface of the first piston body 210 may face the bottom portion 116 of the first container 100. Also, a circumferential surface of the first piston body 210 may face the first side portion 104 of the first container 100. The first piston body 210 may be made of a hard material. For example, the first piston body 210 may be made of, for example, plastic, a metal, etc.

Preferably, in the upper surface of the first piston body 210, a recessed surface 211 may be formed with a predetermined depth. The recessed surface 211 may have a lowest point at the center and be inclined upward in an external diameter direction from the lowest point 212, as seen from above. Meanwhile, the lowest point 212 may be positioned immediately below the third opening 124.

Accordingly, as shown in (a) and (b) of FIG. 4, the upper surface of the first piston body 201 may have a V shape inclined downward towards the center, as seen from a longitudinal cross-section passing the center of the first piston body 210.

However, the shape of the recessed surface 211 is not limited to this. According to some embodiments, a downward recessed groove may be further formed with a deeper depth than that of the recessed surface 211, or the upper surface of the first piston body 210 may have a step or a curve. Furthermore, the lowest point 212 may be positioned at another location of the upper surface, not at the center of the upper surface.

In an upper edge portion and a middle portion of the circumferential surface of the first piston body 210, an upper groove 213 and a middle groove 214 may extend respectively in the circumferential direction, with a predetermined depth in an internal diameter direction. Since the upper groove 213 is formed at the upper edge portion of the first piston body 210, the edge of the upper surface of the first piston body 210 may be recessed to a predetermined depth.

Meanwhile, the lower surface of the first piston body 210 may also have a lower recessed surface 215 recessed upward to a predetermined depth. The lower recessed surface 215 may be in the shape of a circle with a predetermined internal diameter, as seen from below.

The upper ring 220 may be an O ring, which is an O-shaped ring. The upper ring 220 may be made of a material that is different from the first piston body 210, for example, an elastic material such as silicon. The upper ring 220 may be positioned around the upper groove 213 of the upper surface of the first piston body 210 by being tightly inserted in the upper groove 213. Accordingly, the upper ring 220 may configure an upper edge of the first piston 200.

Preferably, as shown in FIG. 4(a), the upper surface of the upper ring 220 may be inclined to protrude upward at the outer portion. Accordingly, the upper surface of the upper ring 220 may have an inclination rising outward in the diameter direction, as seen from the cross-section in a diameter direction.

Since the upper ring 220 having elasticity is formed in the upper outer edge of the first piston 200 and the outer circumference of the upper ring 220 protrudes upward, the upper outer circumferential surface of the first piston 200, specifically, the upper end circumferential surface of the first piston 200 may be in close contact with the first side portion 104 of the first container 100. Accordingly, a material on the first piston 200 may be prevented from leaking below the first piston 200 or from remaining between the upper ring 220 and the first side portion 104 of the first container 100.

Also, when the first piston 200 contacts the top portion 114 of the first container 100, an outer circumferential portion of the upper surface of the first piston 200 may be in close contact with the top portion 114 of the first container 100. Accordingly, when the first piston 200 contacts the top portion 114 of the first container 100, a material remaining on the recessed surface 211 may be collected in the center of the first piston 200, without entering or remaining between the upper outer portion of the first piston 200 and the top portion 114 of the first container 100. Therefore, material extraction efficiency may be improved.

The side ring 230 may also be an O ring, which is an O-shaped ring, and made of a material having elasticity. The side ring 230 may be positioned around the middle groove 214 of the first piston body 210 by being tightly inserted in the middle groove 214. Since the side ring 230 having elasticity is installed around the outer circumferential surface of the first piston 200, the outer circumferential surface of the first piston 200 may be in close contact with the first side portion 104 of the first container 100.

Since the first piston body 210 is made of a hard material and the upper ring 220 and the side ring 230 are made of an elastic material, a service life of the first piston 200 may be lengthened compared with a case in which the entire of the first piston 200 is made of an elastic material, and the first piston 200 may easily move in the inside of the first container 100. In addition, the first piston 200 may be in close contact with the first container 100. Therefore, the processibility, service life, and user convenience of the first piston 200 may be improved, and simultaneously, the extraction efficiency of extracts may be further improved.

The weight 240 may be made of a material having a predetermined weight and a predetermined specific gravity. For example, the weight 240 may be made of a metal material. Accordingly, the weight 240 may apply a proper centrifugal force to the first piston 200 when centrifugation is performed. The weight 240 may be inserted into a weight inserting groove 217 formed in the lower surface of the first piston body 210.

Meanwhile, (b) of FIG. 4 is a modified example of the first piston 200. The first piston 200 may be modified as shown in (b) of FIG. 4.

FIG. 4(b) shows an example in which the first piston 200 includes an upper elastic portion 250 made of an elastic material and a rear body portion 260 made of a hard material. The upper elastic portion 250 may be located in a front portion of the first piston 200, and in an upper surface of the upper elastic portion 250, a recessed surface 252 may be formed. The recessed surface 252 may have a lowest point 254, and in the recessed surface 252, an upward inclination may be at least partially formed in an external diameter direction from the lowest point 254. In an upper outer end of the upper elastic portion 250, a close-contact protrusion 256 may protrude outward. Accordingly, the upper outer circumferential surface of the first piston 200 may be in close contact with the inner wall of the first container 100. Meanwhile, the first piston 200 may also include a side ring 262 and a weight 264.

The first piston 200 shown in FIG. 4(b) may have the same function as the first piston 200 shown in FIG. 4(a), and accordingly detailed descriptions thereof will be omitted.

The upper portion of the first piston 200 may be understood as the front portion of the first piston 200 according to the orientation of the first piston 200 and may be referred to as another term according to the orientation of the first piston 200.

Hereinafter, the elastic body 300 will be described.

The elastic body 300 may be a member having elasticity. The elastic body 300 may be disposed in the inside of the first container 100 and positioned below the first piston 200 to be interposed between the lower surface of the first piston 200 and the bottom portion 116 of the cylinder.

Preferably, the elastic body 300 may be a coil spring. In this case, a lower portion of the elastic body 300 may be positioned in the ring-shaped recessed space 144 to surround the outer circumference of the piston stopper 140, and an upper portion of the elastic body 300 may be positioned in the lower recessed surface 215 formed in the lower recessed surface of the first piston 200.

Meanwhile, as described above, since the cylindrical piston stopper 140 is provided and the elastic body 300 is configured as a coil spring to surround the outer circumference of the piston stopper 140 or the piston stopper 140 is disposed around the outer circumference of the elastic body 300, the elastic body 300 may be prevented from moving to one side. Also, since the piston stopper 140 has a proper height to prevent the first piston 200 from falling excessively to deform the elastic body 300 excessively, the elastic body 300 may maintain elasticity and be prevented from being damaged.

Hereinafter, the first connecting duct 402 and the first control valve 400 will be described.

The first connecting duct 402 may connect the second opening 122 of the first container 100 to the fourth opening 128 of the second container 102. Accordingly, a discharge target material discharged through the second opening 122 may pass through the first connecting duct 402 and be discharged into the second space 112 through the fourth opening 128.

Preferably, at least one part of the first connecting duct 402 may be made of an elastic material to be deformable. For example, the first connecting duct 402 may be a silicon container made of silicon. Accordingly, the first connecting duct 402 may be closed by being pressed and deformed by an external force, and when the external force applied to the first connecting duct 402 is removed, the first connecting duct 402 may be elastically restored to again open.

The first control valve 400 according to an embodiment may be configured as a centrifugal valve that operates by a centrifugal force to open or close the first connecting duct 402. The first control valve 400 may include at least one of a first valve 410 configured as an initial close valve that is closed before a centrifugal force is applied thereto and is opened after a centrifugal force is applied thereto, and a second valve 420 configured as a normal open valve that is opened when no centrifugal force is applied thereto and is closed when a centrifugal force is applied thereto. Details about the configuration of the first control valve 400 will be described below.

Meanwhile, a predetermined base portion 401 having stiffness may be provided to support the first connecting duct 402 when the first control valve 400 deforms the first connecting duct 402. That is, the first connecting duct 402 may be positioned between the first control valve 400 and the base portion 401.

FIG. 5a is an enlarged view showing a structure and operation of the first control valve 400 of the centrifugal separation container according to the first embodiment of the present disclosure, and FIG. 5a is an enlarged view of an area A of FIG. 1. FIG. 5b shows a direction in which a centrifugal force is applied when the centrifugal separation container according to the first embodiment of the present disclosure rotates.

In FIG. 5a, the first valve 410 configured as an initial close valve is shown. (a), (b), and (c) of FIG. 5a show states of before a centrifugal force is applied to the first valve 410, when a centrifugal force is applied to the first valve 410, and after a centrifugal force applied to the first valve 410 is removed, respectively.

The first control valve 400 according to the first embodiment of the present disclosure may include a first valve body 412 and a first rotation shaft 416.

The first valve body 412 may be made of a material with a predetermined weight, for example, a metal. Preferably, at one end of the first valve body 412, a valve tip 414 may protrude.

The first rotation shaft 416 may be coupled with the first valve body 412 such that the first valve body 412 can rotate on the first rotation shaft 416, and the first rotation shaft 416 may be spaced from the center of gravity of the first valve body 412. That is, the first valve body 412 may be eccentric. Accordingly, when a centrifugal force is applied to the first valve body 412, the first valve body 412 may rotate on the first rotation shaft 416.

The first valve body 412 may be rotatably coupled with the first rotation shaft 416 in the state in which the first valve body 412 presses and deforms at least one part of the first connecting duct 402 to thus close the first connecting duct 402. That is, the first valve body 412 may press at least one part of the first connecting duct 402 to close the first connecting duct 402, and at this time, the first valve body 412 may receive an upward elastic force from the first connecting duct 402 located therebelow since the first connecting duct 402 is made of an elastic material. Accordingly, at least one part of the first valve body 412 may be caught between the first connecting duct 402 located therebelow and the first rotation shaft 416, and fixed while pressing and deforming at least one part of the first connecting duct 402 to close it. At this time, the lower portion of the first connecting duct 402 may be supported by the base portion 401 so that the first connecting duct 402 may be caught between the first valve body 412 and the base portion 401 to be closed.

When the first valve body 412 is fixed as described above, the first valve body 412 may keep the first connecting duct 402 closed until a centrifugal force is applied to the first valve body 412 as shown in (a).

Successively, when centrifugation is performed so that a centrifugal force F is applied to the first valve body 412 as shown in (b), a resultant force of the centrifugal force F and an elastic restoring force of the first connecting duct 402 may be applied to the first valve body 412, and accordingly, the first valve body 412 may rotate against the caught force of the first valve body 412. Accordingly, the first valve body 412 may rotate in a direction indicated by an arrow R, and the deformed first connecting duct 402 may be restored to open.

Thereafter, the first valve body 412 may be not restored to the initial position even when the rotation is reduced or stopped, as shown in (c). Accordingly, the first connecting duct 402 may be kept open without being deformed. The reason is because the first connecting duct 402 has elasticity to intend to maintain its original shape and the first valve body 412 is weight-balanced in left and right directions with respect to the rotation shaft 416 so that when the first valve body 412 rotates to horizontality by receiving a centrifugal force at its position closing the first connecting duct 402, the first valve body 412 maintains horizontality to keep opening the first connecting duct 402 even when a centrifugal force continues to be applied to the first valve body 412.

At this time, the centrifugal force may be applied as indicated by an arrow in FIG. 5b. That is, the centrifugal separation container may rotate in a direction indicated by an arrow R with respect to a rotation center (RC). Accordingly, the centrifugal force may have a component applied from the top portion 114 of the centrifugal separation container to the bottom portion 116. That is, the centrifugal force may have a component of moving the first piston 200 downward. However, the direction of the centrifugal force is not limited to the direction toward the bottom portion 115 from the top portion 114, as long as the centrifugal force has a component of a direction toward the bottom portion 116 from the top portion 114.

Since the first valve 410 configured as an initial close valve is included in the first control valve 400, body fluids, tissue, etc. may be, when injected into the first container 100, prevented from leaking out through the first connecting duct 402. Particularly, the first valve 410 may be opened automatically by a centrifugal force when centrifugation starts, and even after the rotation is stopped, the first valve 410 may be kept open so as to easily discharge a discharge target material.

FIG. 6 shows a structure and operation of a first control valve 400 of a centrifugal separation container according to a second embodiment of the present disclosure. According to the second embodiment of the container of centrifugation, the area A of FIG. 1 may have a configuration shown in FIG. 6.

The centrifugal separation container according to the second embodiment of the present disclosure may be similar to the first embodiment, except for a configuration and operation of the first control valve 400.

The centrifugal separation container according to the second embodiment of the present disclosure may include the first control valve 400, wherein the first control valve 400 may include the first valve 410 configured as an initial close valve and the second valve 420 configured as a normal open valve.

The configuration and operation of the first valve 410 configured as an initial close valve have been described above, and accordingly, further descriptions thereof will be omitted.

The second valve 420 may include a second valve body 422 made of a material with a predetermined weight, and a second rotation shaft 426, similarly to the first valve 410. The second valve body 422 may have the predetermined weight and include a second valve tip 424. The second valve body 422 may be rotatably coupled with the second rotation shaft 426, and the second rotation shaft 426 may be spaced from the center of gravity of the second valve body 422. That is, the second valve body 422 may be eccentric.

Accordingly, when a centrifugal force is applied to the second valve body 422, the second valve body 422 may rotate on the second rotation shaft 426. At this time, the second valve tip 424 may press and deform the first connecting duct 402 since a distance between the second rotation shaft 426 and the second valve tip 424 is shorter than a distance between the second rotation shaft 426 and the first connecting duct 402.

The second valve 420 may be different from the first valve 410 in that the second valve body 422 is freely rotatable on the second rotation shaft 426 from the initial position.

As shown in (a) of FIG. 6, when no centrifugal force is applied, the first connecting duct 402 may be maintained in an open state since the first connecting duct 402 has an elastic restoring force although the second valve 420 presses the first connecting duct 402. Thereafter, as shown in (b), when a centrifugal force F is applied, the second valve body 422 may rotate on the second rotation shaft 426 in a direction indicated by an arrow R2 to press and deform the first connecting duct 402, thereby closing the first connecting duct 402. At this time, the first valve 410 may rotate in the direction indicated by the arrow R2 to open the first connecting duct 402. Successively, as shown in (c), when the rotation is reduced or stopped so that the centrifugal force F applied to the second valve body 422 is reduced or no centrifugal force is applied to the second valve body 422, the second valve body 422 may rotate in a direction indicated by an arrow R3 by the elastic restoring force of the first connecting duct 402 to return to the original state, and the first connecting duct 402 may again open. At this time, the first valve 410 may be maintained in an open state, as described above.

As such, by providing the first control valve 400 having both the first valve 410 configured as an initial close valve and the second valve 420 configured as a normal open valve, body fluids, tissue, etc. may be, when injected into the first container 100 before centrifugation, prevented from leaking out unnecessarily. Also, when the rotation is reduced or stopped after centrifugation, the first connecting duct 402 may open, and thereafter, when the centrifugal separation container rotates for a reason of washing, re-separation, etc., the first connecting duct 402 may be automatically closed. Accordingly, the centrifugal separation container may be easily operated and managed.

The centrifugal separation container according to the present disclosure may be modified as shown in FIG. 7.

FIG. 7 shows a longitudinal cross-section of a centrifugal separation container according to a third embodiment of the present disclosure, and FIG. 8 shows operations of the centrifugal separation container.

The centrifugal separation container according to the third embodiment of the present disclosure may be similar to the first embodiment, except for the upper portion 114, the configuration of the first connecting duct 402, and the configuration of the first control valve 400.

Meanwhile, in the third embodiment, the first container 100 and the second container 102 may have a concentric structure, as shown in FIG. 7. However, the first container 100 and the second container 102 may be arranged side-by-side, as shown in FIG. 3. Also, the first container 100 and the second container 102 may be spaced from each other.

The first connecting duct 402 may include a first duct 403 connected to the first container 100 and a second duct 404 connected to the second container 102, and the first duct 403 may be connected to the second duct 404 with a vertical flow path 405 having a predetermined internal diameter in between.

Meanwhile, below the vertical flow path 405, a predetermined expansion space 406 may be formed. Also, above the vertical flow path 405, a valve operating hole 407 may be formed to penetrate the top portion 114 vertically. Meanwhile, in the valve operating hole 407, a predetermined sealing 408 may be provided.

Preferably, as shown in FIGS. 7 and 8, the top portion 114 may have a predetermined thickness to form the first connecting duct 402 therein, and the top portion 114 may be configured with a predetermined member that is coupled with and decoupled from the first side portion 104 and the second side portion 110, although not limited thereto.

The first control valve 400 may be configured with a weight body 431 having a predetermined weight, and a weight valve 430 including an elastic ring 432 disposed around the weight body 431. The elastic ring 432 may be in close contact with an inner wall of the vertical flow path 405 by inserting the weight valve 430 into the vertical flow path 405, thereby closing the vertical flow path 405.

Also, a top end of the weight body 431 may be connected to an operating beam 434 extending upward and passing through the valve operating hole 407 to be exposed to the outside, and a predetermined grip portion 435 may be provided at a top end of the operating beam 434. Meanwhile, the sealing 408 may be in close contact with the operating beam 434 to prevent a material from leaking out.

Operations of the first connecting duct 402 and the first control valve 400 according to the current embodiment will be described below. As shown in FIG. 8a, when no centrifugal force is applied, the weight valve 430 may be inserted into the vertical flow path 405 to close the vertical flow path 405. However, when a centrifugal force is applied downward, the weight valve 430 may escape from the vertical flow path 405 to fall and thus move to the expansion space 406, as shown in FIG. 8b. Accordingly, the first duct 403 may communicate with the second duct 404 so that a material flows through the first and second ducts 403 and 404.

Meanwhile, after the operation is completed, the grip portion 435 may be pulled upward, as necessary. Then, the weight valve 430 may be again inserted into the vertical flow path 405. Accordingly, the weight valve 430 may close the first connecting duct 402.

Meanwhile, FIGS. 9a to 9c show modified examples. In FIGS. 9a and 9b, a predetermined support step 436 may be provided at the top end of the operating beam 434, and between the support step 436 and the top portion 114, a stopper 437 may be provided to limit the operation of the weight valve 430. The stopper 437 may have a structure shown in FIG. 9c. (a) and (b) of FIG. 9c respectively show a side view and a top view of the stopper 437. That is, the stopper 437 may be a block formed in the shape of a rectangular parallelepiped and have a groove 438 in which the operating beam 434 is inserted. When the stopper 437 is positioned between the support step 436 and the top portion 114 as shown in FIG. 9a, the weight valve 430 may not operate and be maintained in a closed state. When the stopper 437 is removed as shown in FIG. 9b, the weight valve 430 may operate as described above.

The weight valve 430 may be provided to prevent a material from moving between the first container 100 and the second container 102. That is, when a material needs to be injected into the inside of the first container 100, without being unnecessarily discharged to the second container 102, the weight valve 430 may prevent a material injected in the first container 100 from being discharged to the second container 102.

Also, the stopper 437 may select whether to operate the weight valve 430.

Another modified example of the centrifugal separation container according to the present disclosure is shown in FIG. 10.

FIG. 10 shows a longitudinal cross-section of a centrifugal separation container according to a fourth embodiment of the present disclosure, FIGS. 11 and 12 show a movement process of a movement target material in a third container of the centrifugal separation container according to the fourth embodiment of the present disclosure, and FIGS. 13 and 14 show modified forms of the centrifugal separation container according to the fourth embodiment of the present disclosure.

The centrifugal separation container according to the fourth embodiment may further include a third container 500, a second piston 510, a second connecting duct 520, and a second control valve 530. Meanwhile, in FIG. 10, like the second embodiment, the second control valve 400 includes the first valve 410 configured as an initial close valve and the second valve 420 configured as a normal open valve, although not limited thereto. That is, the first control valve 400 may have the same configuration as the first embodiment or the third embodiment.

The third container 500 may have a cylindrical configuration having a third space 504 in which a movement target material is injected. As shown in FIG. 10, the first container 100, the second container 102, and the third container 500 may be integrated into one body to construct a triple container 20. Also, the third container 500 may be configured as a member that is separated from the first container 100 and the second container 102.

Meanwhile, as shown in FIG. 10, the triple container 20 may have a structure in which the first container 100 is positioned in the center of the triple container 20 and the third container 500 and the second container 102 are positioned to both sides of the triple container 20. However, an embodiment in which the third container 500 is coupled with the double container 10 of the first embodiment by an arbitrary method to form an arbitrary structure is also possible. Also, the first control valve 400 may have various structures. The various structures will be described in detail, below.

The first container 100 and the second container 102 may be the same as those of the first embodiment, except that the top portion 114 and the bottom portion 116 extend to the third container 500, a sixth opening 134 for a movement target material is further formed above the first space 108, and the first space 108 and the second space 112 are located side-by-side, instead of being located in a concentric double pipe structure, and accordingly, overlapping descriptions about the first container 100 and the second container 102 will be omitted.

The third container 500 may include a third side portion 502 whose upper and lower ends are respectively coupled with the top portion 114 and the bottom portion 116.

The third side portion 502 may be in the shape of a predetermined standing bucket whose upper and lower ends are respectively coupled with the top portion 114 and the bottom portion 115. Accordingly, an inside cavity of the third side portion 502 may form the third space 504 of the third container 500. The third side portion 502 may be made of, preferably, a transparent material to show the inside.

The top portion 114 may extend to the upper end of the third side portion 502 to cover the first space 108, the second space 112, and the third space 504, and the top portion 114 may further include the sixth opening 134 formed above the first space 108 and a seventh opening 506 formed above the third space 504, in addition to the first opening 120, the second opening 122, the third opening 124, the fourth opening 128, and the fifth opening 130.

The seventh opening 506 may form a passage through which a movement target material is injected into the first space 108. Also, the seventh opening 506 may be in the form of a hole vertically penetrating the top portion 114 above the third space 504. Meanwhile, an intermediate connection portion (not shown) may be provided in the shape of a pipe vertically penetrating the bottom portion 114 above the third space 504, instead of the seventh opening 506, and details about the intermediate connection portion will be described later.

The second piston 510 may be positioned in the inside of the third container 500 in such a way to be movable vertically. The second piston 510 may include a second piston body 512 having a vertical through hole 514 that vertically penetrates the second piston body 512, a side sealing 516, and a weight body 518.

The second piston body 512 may construct a main body of the second piston 510 and may be made of a material having a predetermined weight and a predetermined specific gravity to push and press a movement target material filled therebelow when a centrifugal force is applied thereto.

The second piston 510 may have the vertical through hole 514 that vertically penetrates the second piston body 512.

The side sealing 516 may be disposed around an outer circumference of the second piston body 512 to cause the second piston 510 to be in close contact with an inner side surface of the third container 500. In the outer circumference of the second piston 510, a predetermined installation groove may be formed to fix the side sealing 516.

The weight body 518 may be a member having a predetermined weight to provide the second piston 510 with a greater centrifugal force. The weight body 518 may be inserted on the second piston body 512 or overlap the second piston body 512.

The second connecting duct 520 may include a first line 522 and a second line 524 and further include a third line 526.

One end of the first line 522 may be exposed to the outside through the seventh opening 506 formed in the top portion 114 to be connected to the second control valve 530 as described later, and the other end of the first line 522 may be connected to the vertical through hole 514 of the second piston 510. According to an example, the first line 522 may be made of a soft material and configured as a deformable hose. According to another example, an embodiment in which the first line 522 is configured as a predetermined pipe extending directly downward and protruding below the second piston 510, a space between the vertical through hole 514 and the first line 522 is sealed, and the second piston 510 is movable vertically along the first line 522 is also possible.

Meanwhile, according to an example, an intermediate connection portion (not shown) may be provided in the shape of a pipe vertically penetrating the upper end of the third container 500, instead of the seventh opening 506. Also, an embodiment in which a soft connecting hose is positioned in the inside of the third container 500 to connect a lower end of the intermediate connection portion to the vertical through hole 514, and a predetermined connecting pipe is provided to connect the top end of the intermediate connection portion to the second control valve 530 is possible. In this embodiment, the intermediate connection portion may mediate a connection of the hose and the pipe, and the first line 522 may be configured as a combination of the pipe, the intermediate connection portion, and the hose.

One end of the second line 524 may be connected to the second control valve 530, and the other end of the second line 524 may be connected to the sixth opening 134. The second line 524 may include a one-way valve 534 to prevent a movement target material from flowing backward.

One end of the third line 526 may be connected to predetermined injection means U, and the other end of the third line 526 may be connected to the second control valve 530.

The second control valve 530 may open or close the second connecting duct 520. More specifically, the second control valve 530 may be positioned on the second line 524 and configured as the one-way valve 534 for causing a movement target material to flow toward the first container 100 from the third container 500 while preventing the movement target material from flowing backward. Also, preferably, a three-way valve 532 may be connected to the first line 522, the second line 524, and the third line 526.

Hereinafter, a principle of injecting a movement target material through the third container 500 will be described with reference to FIGS. 11 and 12.

As shown in FIG. 11, when a movement target material W is injected into the third container 500, the three-way valve 532 may open to connect the third line 526 to the first line 522. Accordingly, the movement target material W may be injected below the second piston 510 through the third line 526 and the first line 522 from the injection means U, in a direction indicated by an arrow A. At this time, the second piston 510 may be pushed upward to move up as indicated by an arrow B.

After the movement target material W is completely injected, the three-way valve 532 may be turned to connect the first line 522 to the second line 524.

Successively, as shown in FIG. 12, when the centrifugal separation container rotates in a direction indicated by an arrow R, a centrifugal force may be applied toward the bottom portion 116 of the centrifugal separation container with respect to a rotation center RC, as indicated by an arrow F. Accordingly, the second piston 510 may move downward by receiving the centrifugal force, as indicated by an arrow M, and accordingly, the second piston 510 may push and press the movement target material filled below the second piston 510 to generate positive pressure. The rotation center RC of the centrifugal separation container may have a direction directly toward the ground from above the centrifugal separation container.

The centrifugal force may be also applied to the first piston 200 located in the inside of the first container 100. Accordingly, when the first piston 200 moves downward as indicated by an arrow N, negative pressure may be temporarily generated in a space above the first piston 200 in the first container 100, the first line 522, and the second line 524. Accordingly, the positive pressure applied to the movement target material and the negative pressure formed in the space above the first piston 200, the first line 522, and the second line 524 may be simultaneously applied to the movement target material. When the positive pressure and the negative pressure are simultaneously applied to the movement target material, the movement target material may move to the first container 100 against the centrifugal force applied to the movement target material in a part of the first line 522.

The simultaneous application of the negative pressure and the positive pressure may cause an effect as follows.

The movement target material located below the second piston 510 in the third container 500 may be applied a downward centrifugal force. Also, the movement target material filled in the first line 522 and the second line 524 may be applied the downward centrifugal force. As such, a movement target material in the third container 500 and a movement target material filled in at least one part of the first line 522 and the second line 524 may be applied a centrifugal force in a direction which is against a movement direction from the third container 500 to the first container 100. Accordingly, the movement target material may hardly move or may not move.

However, as described above, since negative pressure and positive pressure are simultaneously applied to the movement target material, the movement target material may become movable against the centrifugal force applied in the direction that is opposite to the movement direction of the movement target material. At this time, the movement target material may be injected from the third container 500 to the first container 100 through the first line 522 and the second line 524, as indicated by an arrow W of FIG. 12. As described above, the weight body 518 included in the second piston 510 and the weight 240 included in the first piston 510 may amplify a centrifugal force to further reinforce a pushing force of the second piston 510 and a pulling force of the first piston 200. Accordingly, the movement target material may be more smoothly injected.

Meanwhile, the centrifugal separation container according to the current embodiment of the present disclosure further including the third container 500 may be modified as shown in FIGS. 13a to 13c. FIGS. 13a to 13c show traverse cross-sections of modified forms of the centrifugal separation container according to the fourth embodiment of the present disclosure.

FIG. 13a shows an embodiment in which the first container 100 and the third container 500 are arranged side-by-side in the second space 112 of the second container 102. In this embodiment, the centrifugal separation container may have a minimum volume, and in some cases, the second container 102 may be in the shape of a bucket and include predetermined fixing means for fixing the first container 100 and the third container 500 therein.

However, any other combinations of the first container 100, the second container 102, and the third container 500 are also possible as long as any two of the first container 100, the second container 102, and the third container 500 are arranged side-by-side and the remaining one surrounds the containers arranged side-by-side.

In the current embodiment, since the second space 112 is provided outside the first container 100 and the third container 500 so that a discharge target material is discharged to the second space 112, the centrifugal separation container may be easily balanced. That is, a discharge target material may be disposed around the outer circumferences of the first container 100 and the third container 500 to prevent the center of gravity of the centrifugal separation container from being biased to one side. Accordingly, the entire container coupling structure including the centrifugal separation container according to the present disclosure may more efficiently perform centrifugation.

Meanwhile, another embodiment is shown in FIG. 13b. In the embodiment of FIG. 13b, the first to third containers 100, 102, and 500 may have a triple container form of a concentric structure. As such, the third to third containers 100, 102, and 500 may be arranged side-by-side or arranged in a concentric structure in which each container is positioned in another container. Also, the first to third containers 100, 102, and 500 may be arranged in the shape of an equilateral triangle, as shown in FIG. 13c.

Meanwhile, an embodiment in which a predetermined bucket is provided to accommodate and couple at least one or two of the first container 100, the second container 102, and the third container 500 is also possible.

Meanwhile, the centrifugal separation container according to the present disclosure further including the third container 500, as shown in the above-described embodiment, may be modified to forms shown in FIGS. 14a and 14b. FIGS. 14a and 14b show other modified forms of the centrifugal separation container according to the fourth embodiment of the present disclosure. In FIGS. 14a and 14b, the first control valve 400 included in the first connecting duct 402 connecting the first container 100 to the second container 102 is configured as the weight valve 430 described above with reference to the third embodiment. However, in FIGS. 14a and 14b, a one-way valve 430A may be further provided, in addition to the weight valve 430, to prevent a back flow from the second container 102 to the first container 100. Since the remaining components are the same as those described above, detailed descriptions thereof will be omitted.

FIG. 15 shows a longitudinal cross-section of a centrifugal separation container according to a fifth embodiment of the present disclosure, and (a) and (b) of FIG. 16 show an operation of the first control valve 400 of the centrifugal separation container according to the fifth embodiment of the present disclosure. The fifth embodiment is similar to the fourth embodiment except that the first control valve 400 includes a one-way valve 440 and a rotation valve 450. Meanwhile, in FIG. 15, like the fourth embodiment, the third container 500, the second piston 510, the second connecting container 520, and the second control valve 530 are provided, although not limited thereto. Like the first embodiment or the second embodiment, an embodiment in which the first container 100 and the second container 102 are provided without the third container 500 is also possible.

The first control valve 400 according to the fifth embodiment may include the one-way valve 440 included in the second opening 122, and the rotation valve 450 for opening and closing the first connecting duct 402.

The one-way valve 440 may be included in the second opening 122 formed in the top portion 114 of the first container 100. The one-way valve 440 may allow a flow in a direction from the first container 100 to the second container 200 and disallow a flow in the opposite direction.

The rotation valve 450 may include a valve hammer and an elastic member 460 for elastically biasing the valve hammer 452.

The valve hammer 452 may include a valve rod 454 having a predetermined length, a pressing head 456 formed at one end of the valve rod 454, located above the first connecting duct 402 and having a predetermined weight, and a rotation shaft 458 disposed at the other end of the valve rod 454, and the valve hammer 452 may be configured to be rotatable on the rotation shaft 458. The rotation shaft 458 may be connected to a predetermined connecting member 462 mounted on the second container 200, for example, as shown in FIG. 15. For example, the valve rod 454 may rotate with an inclined angle with respect to the top portion 114 of the second container 200. Meanwhile, a part of the valve hammer 452 contacting the first connecting duct 402 may include a pressing head 456 for easily pressing and deforming the first connecting duct 402.

The elastic member 460 may elastically bias the pressing head 456 of the valve hammer 452 upward. The elastic member 460 may be positioned between the rotation shaft 458 and the pressing head 456 to elastically bias the valve rod 454 upward to apply an upward force to the pressing head 456. In FIG. 15, the elastic member 460 is located on the top portion 114 of the second container 200, although not limited thereto.

An operation of the rotation valve 450 will be described with reference to FIGS. 15 and 16. When no centrifugal force is applied as shown in FIG. 15, the first connecting duct 402 may be not closed due to an upward elastic force of the elastic member 460 and an elastic restoring force of the first connecting duct 402 although the pressing head 456 is positioned on the first connecting duct 402. However, when the centrifugal separation container rotates for centrifugation, as shown in (a) of FIG. 16, a centrifugal force F may be applied downward to the pressing head 456 having a great weight, so that the pressing head 456 rotates in a direction indicated by an arrow F2. Accordingly, the pressing head 456 may press and deform the first connecting duct 402 to close the first connecting duct 402. Successively, when the rotation of the centrifugal separation container stops and no centrifugal force is applied as shown in (b), the pressing head 456 may move upward by the elastic member 460 as indicated by an arrow F3 to return to its original position, and the first connecting duct 402 may again open by the elastic restoring force. Accordingly, the rotation valve 450 may be configured as a normal open valve. Meanwhile, in FIG. 16, the third opening cap 126 is shown to be openable.

FIG. 17 shows a cross-section taken along line Y-Y of FIG. 15, (a) of FIG. 18 shows a cross-section taken along line X-X of FIG. 15, and (b) of FIG. 18 is a front view of a piston position controller 600.

The centrifugal separation container according to the fifth embodiment of the present disclosure may further include the piston position controller 600, and in at least one part of the first side portion 104 of the first container 100, a side hole 105 may be formed, and in at least one part of a side surface of the first piston 200, a side groove 261 may be formed.

FIG. 17 is a cross-section view taken along line Y-Y of FIG. 15, and in the centrifugal separation container according to the fifth embodiment of the present disclosure, at least one side portion of the first container 100 may be preferably exposed to the outside such that the piston position controller 600 as described later is installed in the first container 100 to control operations of the first piston 200.

FIG. 18(a) is a cross-sectional view taken along line X-X of FIG. 15, and the piston position controller 600 according to the fifth embodiment may be applied to various embodiments, other than the embodiment in which the third container 500 is provided, the embodiment in which the first control valve includes both the first valve and the second valve, or the embodiment in which the first control valve includes the one-way valve 440 and the rotation valve 450. That is, the piston position controller 600 may be also applied to the first, second, and third embodiments described above. Also, FIG. 18(b) is a front view of the piston position controller 600 and is a view of when FIG. 18(a) rotates in a counterclockwise direction.

The current embodiment is the same as the above-described embodiments, except that the piston position controller 600 is provided, that the side hole 105 is formed in the side portion 104 of the first container 100, and that the side groove 261 is formed in the side portion of the piston 200, and accordingly, overlapping descriptions will be omitted.

In the side portion 104 of the first container 100, the side hole 105 may be formed in an internal diameter direction of the first container 100 to penetrate the first container 100. Preferably, the side hole 105 may be formed in a lower part of the side portion 104.

In the side surface of the first piston 200, the side groove 261 may be formed to be recessed in an internal diameter direction of the first piston 200. Preferably, a part of the outer circumferential surface of the first piston body 210 may be recessed to form the side groove 261. Accordingly, when the piston 200 falls to arrive at a location at which the side hole 105 is formed, the side groove 261 may be exposed in the side direction through the side hole 105.

The piston position controller 600 may be a member for fixing or unfixing the piston 200 and may be configured with a latch 610, releasing means S, and a lower elastic body 640. Also, the releasing means S may include a link portion 620 and a release weight portion 630, and a bracket 650 for coupling the latch 610, the releasing means S, and the lower elastic body 640 may be further included.

The latch 610 may include a locking beam 612, a rotating shaft 614, and a locking protrusion 616.

The locking beam 612 may be configured in the form of a beam extending vertically. The rotation shaft 614 may be positioned at an upper end of the locking beam 62, and the locking beam 612 may rotate with an inclined angle with respect to the side portion 104 of the first container 100 on the rotation shaft 614. The locking protrusion 616 may be formed in a middle portion of the locking beam 612 and protrude to the inside direction of the first container 100 to protrude to the first space 108 through the side hole 105.

Since the locking beam 612 is rotatable on the rotation shaft 614, the latch 610 may rotate between a catch position at which the locking protrusion 616 protrudes to the inside of the first container 100 through the side hole 105 and a release position at which the locking protrusion 616 departs from the first container 100. When the latch 610 is located at the catch position, the locking protrusion 616 may be locked on the side groove 216 of the piston 200.

At least a part of the release means S may lie in a horizontal direction on a lower portion of the locking beam 612. The release means S may move between a first position at which it pushes the lower end of locking beam 612 outward to move the latch 610 to the release position and a second position for moving the latch 610 to the catch position. When no centrifugal force is applied, the lower elastic body 640 may elastically bias the release means S so that the release means S moves to the second position.

More specifically, the release means S may include the link portion 620 and the release weight portion 630.

The link portion 620 may include an upper arm 622, a lower arm 624, and a center shaft 626.

The upper arm 622 may be disposed below the latch 610, and as seen from the side direction, the upper arm 622 may be positioned inward with respect to the lower end of the locking beam 612. The lower arm 624 may extend obliquely outward and downward with respect to the upper arm 622, and the upper arm 622 and the lower arm 624 may be bent with a predetermined inclined angle. The center shaft 626 may be positioned between the upper arm 622 and the lower arm 624 such that the upper arm 622 and the lower arm 624 perform a seesaw motion with respect to the center shaft 626. Accordingly, when the lower arm 624 moves inward with respect to the first container 100, the upper arm 622 may move outward with respect to the first container 100 to push the lower end of the locking beam 612 outward. When the lower arm 624 returns to its original position, the upper arm 622 may return to its original position, and accordingly, the locking beam 612 may also return to its original position.

The release weight portion 630 may be made of a material having a weight to apply a centrifugal force and disposed around the outer surface of the lower arm 624. In an inner surface of the release weight portion 630, that is, in a surface of the release weight portion 630 facing the lower arm 624, a groove 632 may be formed into which at least one part of the lower arm 624 can be inserted. Preferably, at the upper portion of the groove 632, an upward inclined surface may be formed to correspond to an inclination of the lower arm 624.

The release weight portion 630 may move between an upper position at which the lower arm 624 is accommodated in the groove 632 and a lower position at which the release weight portion 630 pushes the lower arm 624 inward. Herein, the upper position may be a position at which the release weight portion 630 is located at the upper position so that the lower arm 624 is accommodated in the groove 632 so as not to be pushed by the release weight portion 630, and the lower position may be a position at which the release weight portion 630 moves downward so as to push the lower arm 624 inward. Accordingly, the release weight portion 630 may move up and down as indicated by an arrow L of FIG. 18(b).

The lower elastic body 640 may elastically bias the release weight portion 630. As shown in FIG. 18(a), the lower elastic body 640 may elastically bias the release weight portion 630 upward to move the release weight portion 630 from the lower position to the upper position, and when no external force is applied, the lower elastic body 640 may maintain the release weight portion 630 at the upper position.

The bracket 650 may be a member for coupling the piston position controller 600 with the first container 100. The bracket 650 may support the lower elastic body 640 upward and guide the weight to be movable vertically. The rotation shaft 614 of the latch 610 and the center shaft 626 of the link portion 620 may be connected to the bracket 650. Accordingly, the bracket 650 may include a predetermined guide portion for guiding an up-down movement of the release weight portion 630, and in the release weight portion 630, a predetermined guide groove may extend vertically. Also, the bracket 650 may include an aperture punched in the side direction such that the latch 610 and the link portion 620 rotate in the aperture, and a part to which the rotation shaft 614 and the center shaft 626 are connected.

By providing the piston position controller 600, for example, when body fluids and tissue are injected into the first container 100 so that the piston 200 falls to a position at which the piston position controller 600 is located, the piston 200 may be locked by the latch 610 to be maintained at the position. Meanwhile, when centrifugation starts so that the centrifugal separation container rotates, the piston 200 may be unlocked. Accordingly, during a process of centrifugation, a material may be easily injected, discharged, and extracted, and a movement target material may also be easily injected and discharged.

FIG. 19 shows a longitudinal cross-section of a centrifugal separation container according to a sixth embodiment of the present disclosure. The sixth embodiment shown in FIG. 19 may further include a bucket 700 in which the first container 100, the second container 200 and the third container 500 are accommodated and coupled with each other, compared with the fifth embodiment shown in FIG.

16. Also, the sixth embodiment shown in FIG. 19 may be different from the fifth embodiment shown in FIG. 16 in that the rotation valve 450 is connected to the bucket 700. That is, in at least one part of the bucket 700, a connection member 702 to which the rotation shaft 458 of the rotation valve 450 is connected may be provided such that the rotation valve 450 is connected to the bucket 700 to operate. By providing the bucket 700, the first container 100, the second container 200, and the third container 500 may be integrated into one body although configured as separate members, and the rotation valve 450 may also be connected to the bucket 700, thereby achieving a more compact configuration.

Meanwhile, in FIG. 19, the bucket 700 may accommodate the triple container 20 including all of the first container 100, the second container 102, and the third container 500. However, an embodiment in which the bucket 700 accommodates and couples at least one or two of the first container 100, the second container 102, and the third container 500 is also possible. That is, the bucket 700 may be applied to all of the above-described embodiments.

FIG. 20 shows a coupling structure of the bucket 700 and the centrifugal separation container according to an embodiment of the present disclosure, (a) of FIG. 21 shows a longitudinal cross-section of a bucket coupled with a centrifugal separation container according to an embodiment of the present disclosure, (b) of FIG. 21 shows a cross-section taken along line X-X of (a) of FIG. 21, FIG. 22 shows a coupling structure of a centrifugal separation container according to an embodiment of the present disclosure, configured by coupling a bucket with a rotation body, and FIG. 23 shows a coupling structure of a centrifugal separation container according to an embodiment of the present disclosure, configured by coupling the centrifugal separation container, a bucket, and a rotation body. Meanwhile, the centrifugal separation container shown in FIG. 23 has the same structure as the centrifugal separation container according to the fourth embodiment of the present disclosure, although not limited thereto.

Referring to FIG. 20, the bucket 700 may include a storage box 710 in which a storage space 712 is formed, and the triple container 20 may be inserted into and accommodated in the storage space 712. However, another type of a centrifugal separation container, instead of the triple container 20, may be accommodated in the storage space 712.

A corner of the storage space 712 may be inclined to form a predetermined cutting portion 714, and the triple container 20 may have an inclined corner 21 to correspond to the predetermined cutting portion 714 so that a user can insert the triple container 20 into the storage space 712 at an exact position. However, the present disclosure is not limited to forming the cutting portion 714 and the inclined corner 21, as long as the storage space 712 has a shape corresponding to the triple container 20 and the storage space 712 and the triple container 20 have asymmetric shapes so that a user can recognize directivity when inserting the triple container 20 into the storage space 712.

In the upper end of the storage box 710, a predetermined connecting portion 720 may be provided to protrude outward, at least, in both side directions. In the connecting portion 720, a predetermined first connecting groove 722 and a predetermined second connecting groove 724 having different sizes may be formed. The first connecting groove 722 and the second connecting groove 724 may be respectively formed in both sides of the storage box 710 with the storage box 710 in between, and may be recessed upward from the bottom of the connecting portion 720 and open outward. Also, the first connecting groove 722 and the second connecting groove 724 may have different sizes. Also, the first connecting groove 722 and the second connecting groove 724 may be concentric to each other and have a curved surface such that the bucket 700 is rotatable on the first connecting groove 722 and the second connecting groove 724.

As shown in FIG. 22, a predetermined rotation body 2 with which a plurality of centrifugal separation containers 1 are coupled to rotate may be provided. The rotation body 2 may have a rotation center shaft R and rotate on the rotation center shaft R. The rotation body 2 may have a plurality of connecting arms 4 extending radially in the external circumferential direction from the rotation center shaft R.

At least one of the plurality of centrifugal separation containers 1 may be positioned between two neighbouring ones of the connecting arms 4 and connected to the neighbouring connecting arms 4.

Also, the connecting arms 4 may include a first connecting protrusion 5 and a second connecting protrusion 6 that are respectively connected to the first connecting groove 722 and the second connecting groove 724 formed in the connecting portion 720 positioned in the upper end of the bucket 700. The first connecting protrusion 5 and the second connecting protrusion 6 may have sizes corresponding to the first connecting groove 722 and the second connecting groove 724, wherein the first connecting protrusion 5 may be connected to the first connecting groove 722 and the second connecting protrusion 6 may be connected to the second connecting groove 724. Accordingly, the centrifugal separation container 1, which is a combination of the bucket 700 and the triple container 20, may be connected to the rotation body 2 with directivity through the first connecting groove 722, the second connecting groove 724, the first connecting protrusion 5, and the second connecting protrusion 6, thereby implementing a coupling structure 3 of the centrifugal separation container 1. In addition, the first connecting protrusion 5 and the second connecting protrusion 6 may be concentric to each other. Accordingly, when the first connecting groove 722 and the second connecting groove 724 of the bucket 700 are connected to the first connecting protrusion 5 and the second connecting protrusion 6, the bucket 700 may rotate on the first connecting protrusion 5 and the second connecting protrusion 6. Accordingly, when the rotation body 2 rotates on the rotation center shaft R, the centrifugation tubs 1, coupled as shown in FIG. 22, may rotate by a centrifugal force in the state in which the bottom portions 116 are positioned in the external diameter direction with respect to the rotation center shaft R, as shown in FIG. 23.

Referring to FIGS. 22 and 23, the coupling structure 3 of the centrifugal separation containers 1 may be a point symmetry structure with respect to the rotation center shaft R. That is, the coupling structure 3 may have an arrangement of a crossing symmetry with respect to horizontal and vertical central axes passing the rotation center shaft R. That is, the centrifugal separation containers 1 may face each other such that the same kind of containers may be positioned at locations A1 and A2 that are symmetric to each other with respect to the rotation center shaft R. For example, when the current embodiment is applied to the triple container 20, the second container 102 may be positioned at the locations A1 and A2, as shown in FIG. 23.

As such, by providing an arrangement of a symmetric structure with respect to the rotation center shaft R, the coupling structure of the centrifugal separation container according to the present disclosure may be more advantageous in view of weight balance when a movement target material moves and a discharge target material is discharged.

Hereinafter, operations of a centrifugal separator including the centrifugal separation container according to the fourth embodiment of the present disclosure will be described sequentially with reference to FIGS. 24 to 27. For convenience of description, in FIGS. 24 to 27, the centrifugal separation container 1 is shown in the state which the bottom portion 116 is positioned in the external diameter direction with respect to the rotation center shaft R, like when the rotation body 2 rotates.

Figure 24:
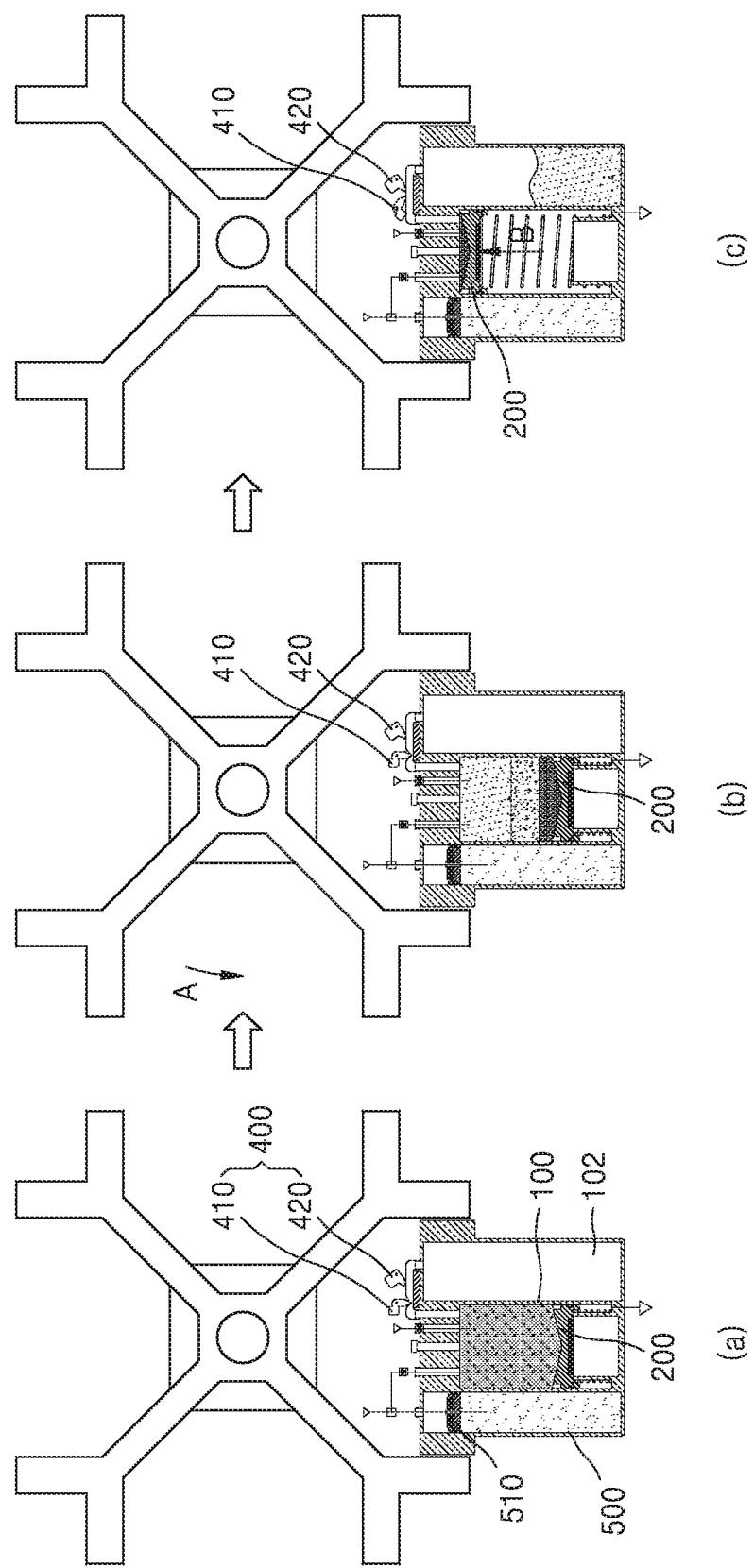

As shown in (a) of FIG. 24, the centrifugal separation container 1 may be installed in the rotation body 2 to construct a coupling structure of the centrifugal separation container 1. Then, a movement target material may be filled in the third container 500, and body fluids and tissue may be filled in the first container 100. When the movement target material, the body fluids, the tissue, etc. are injected, the second piston 510 in the third container 500 may rise, and the first piston 200 in the first container 100 may fall, as shown in (a).

At this time, the first control valve 400 may have an initial close valve so that the first connecting duct 402 may be closed.

Successively, as shown in (b), first centrifugation may be performed. When the rotation body 2 rotates in a direction indicated by an arrow A of FIG. 24(b), the centrifugal separation container 1 may rotate in the state in which the bottom portion 116 is positioned in the external diameter direction with respect to the rotation center shaft R, and accordingly, a centrifugal force may be applied in the external diameter direction. During the first centrifugation, the first control valve 400 may be closed by receiving the centrifugal force. Meanwhile, when the first control valve 400 has the first valve 410 and the second valve 420 as described above, the first valve 410 may be opened and the second valve 420 may be closed.

As shown in (c) of FIG. 24, when the first centrifugation terminates and the rotation body 2 stops rotating or decelerates, the second valve 420 may also open by the elasticity of the first connecting duct 402.

Simultaneously, the first piston 200 may move upward as indicated by an arrow B by an elastic force of the elastic body 300 so that a discharge target material may be discharged.

At this time, the front end circumferential surface of the first piston 200 may be in close contact with the inner wall of the first container 100 by the upper ring 220 or the upper elastic portion 250 provided in the first piston 200, so that no material located in front of the first piston 200 is lost. Also, at least a part of the upper surface of the first piston 200 may have a recessed surface 211 with an upward inclination towards the external diameter direction so that a material having a greatest specific gravity remains in the recessed surface 211 of the first piston 200.

At this time, the first control valve 400 may open fully to discharge a material from the first container 100 to the second container 102 through the first connecting duct 402.

Meanwhile, according to the other embodiments, when the first control valve 400 is the first valve 410 configured as an initial close valve, when the first control valve 400 is configured with the rotation valve 450 and the one-way valve 440, or when the first control valve 400 is configured with the weight valve 430 and the one-way valve 430A, likewise, the first control valve 400 may open to discharge a material from the first container 100 to the second container 102 through the first connecting duct 402.

Figure 25:
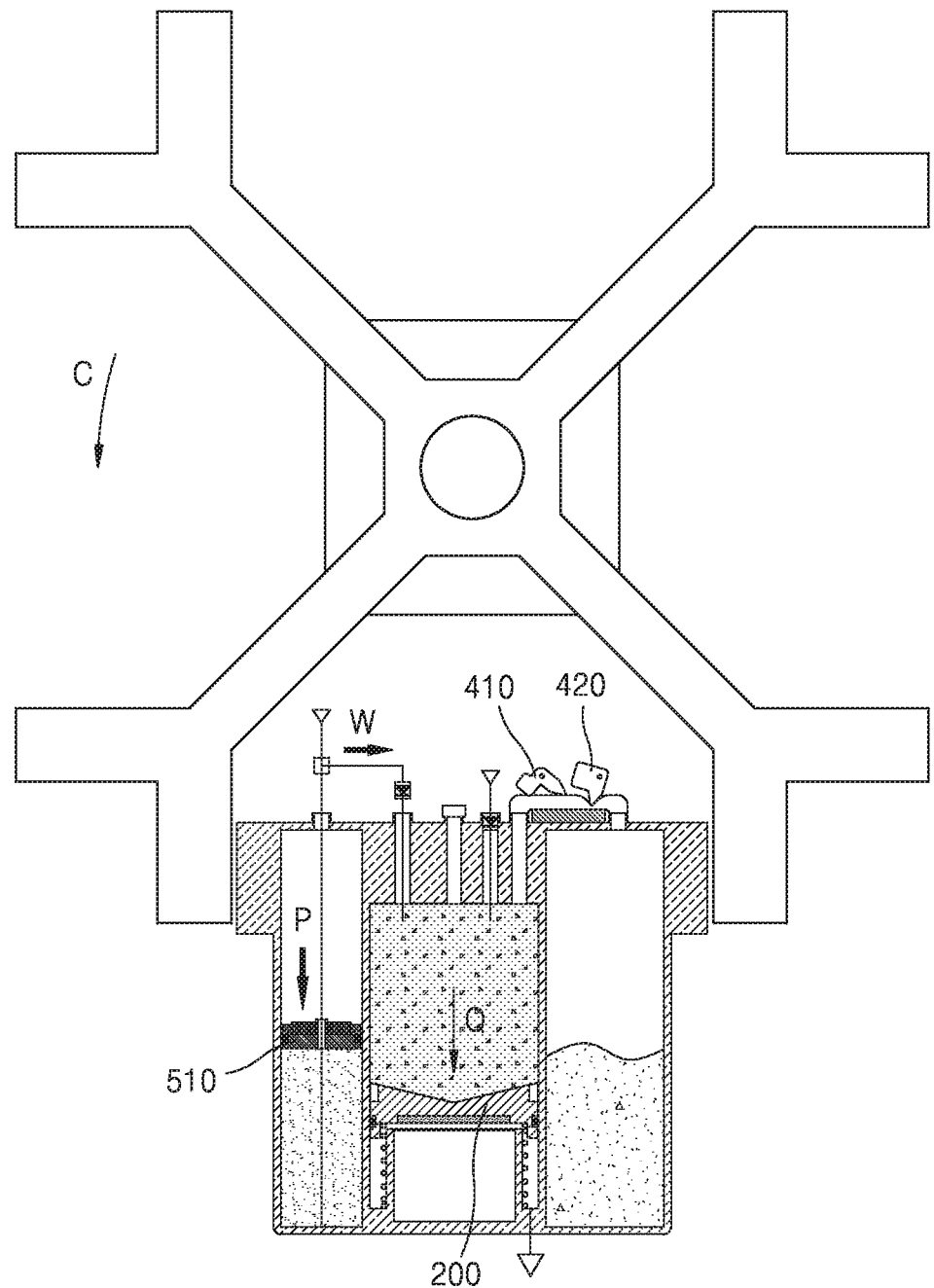

Successively, as shown in FIG. 25, the centrifugal separator may rotate or accelerate in a direction indicated by an arrow C to move the movement target material to the inside of the first container 100. At this time, the movement target material may move as described above. That is, the second piston 510 may fall in a direction indicated by an arrow P by receiving a downward centrifugal force to apply positive pressure to the movement target material filled below the second piston 510, and simultaneously, the first piston 200 may fall in a direction indicated by an arrow Q to generate negative pressure. The positive pressure and the negative pressure may interact so that the movement target material may be injected in a direction indicated by an arrow W against a centrifugal force received in a part of the second connecting duct 520.

As described above, the weight body included in the second piston 510 and the weight 240 included in the first piston 200 may amplify the centrifugal force to further reinforce falling forces of the second piston 510 and the first piston 200, thereby reinforcing the positive pressure formed in the third container 500 and the negative pressure formed in the first container 100. At this time, the first control valve 400 may be in a closed state by the centrifugal force.

Figure 26:
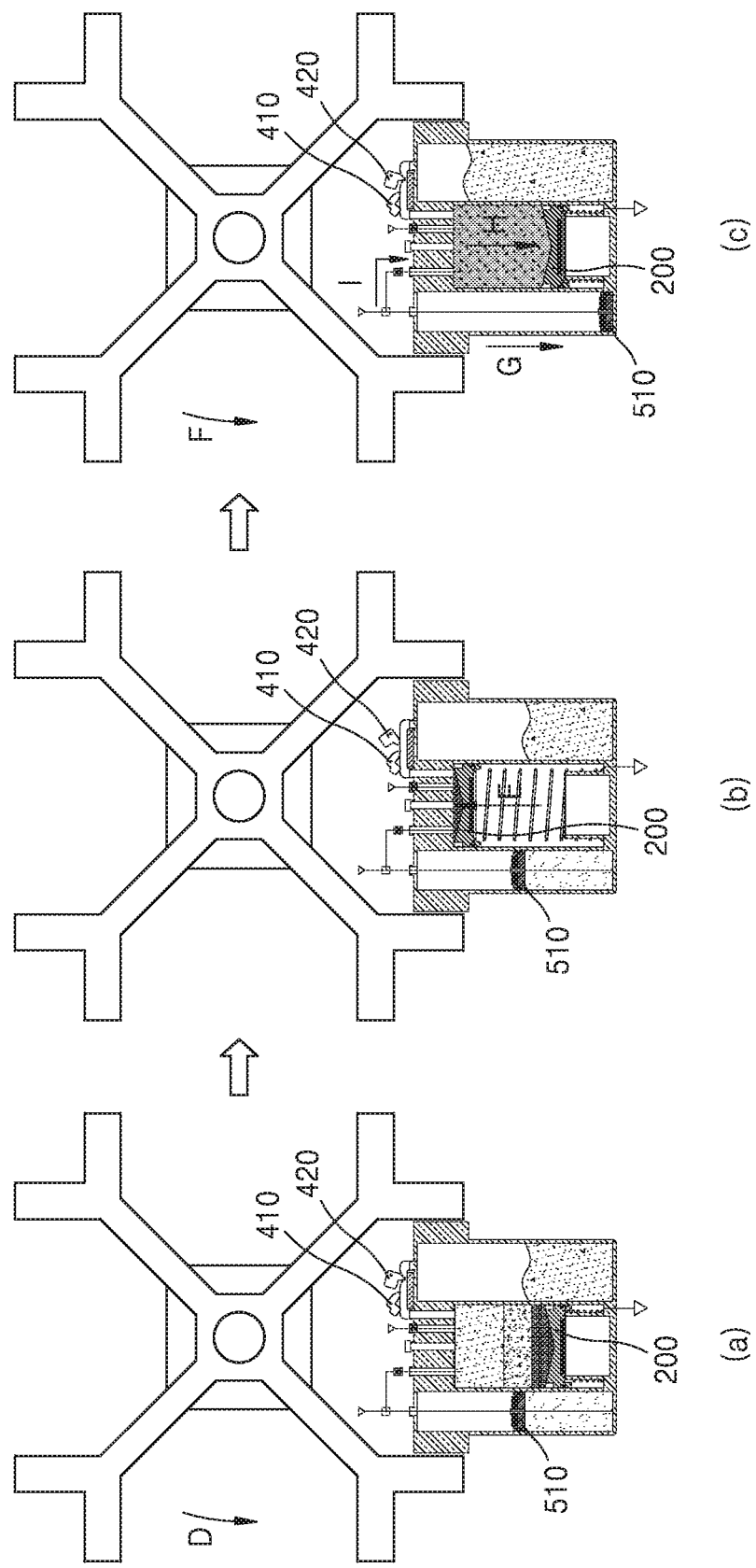

Thereafter, as shown in (a) of FIG. 26, when the first container 100 is fully filled, no negative force may be formed in the inside of the first container 100 so that the movement target material is no longer injected in the first container 100, and second centrifugation may be performed. In this process, the material remaining in the first container 100 and the movement target material may be mixed, washed, and separated. At this time, the first control valve 400 may be in a closed state.

Then, as shown in (b), when the centrifugal separator stops rotating or decelerates, the first piston 200 may rise as indicated by an arrow E so that second discharge may be performed.

At this time, the first control valve 400 may be in an open state.

Successively, as shown in (c), the centrifugal separator may again rotate in a direction indicated by an arrow F to inject the movement target material. The process may be performed in the same manner as described above with reference to FIG. 25. That is, the second piston 510 and the first piston 200 may fall as indicated by arrows G and H so as to inject the movement target material in a direction indicated by an arrow I. At this time, the first control valve 400 may be in a closed state.

Figure 27:
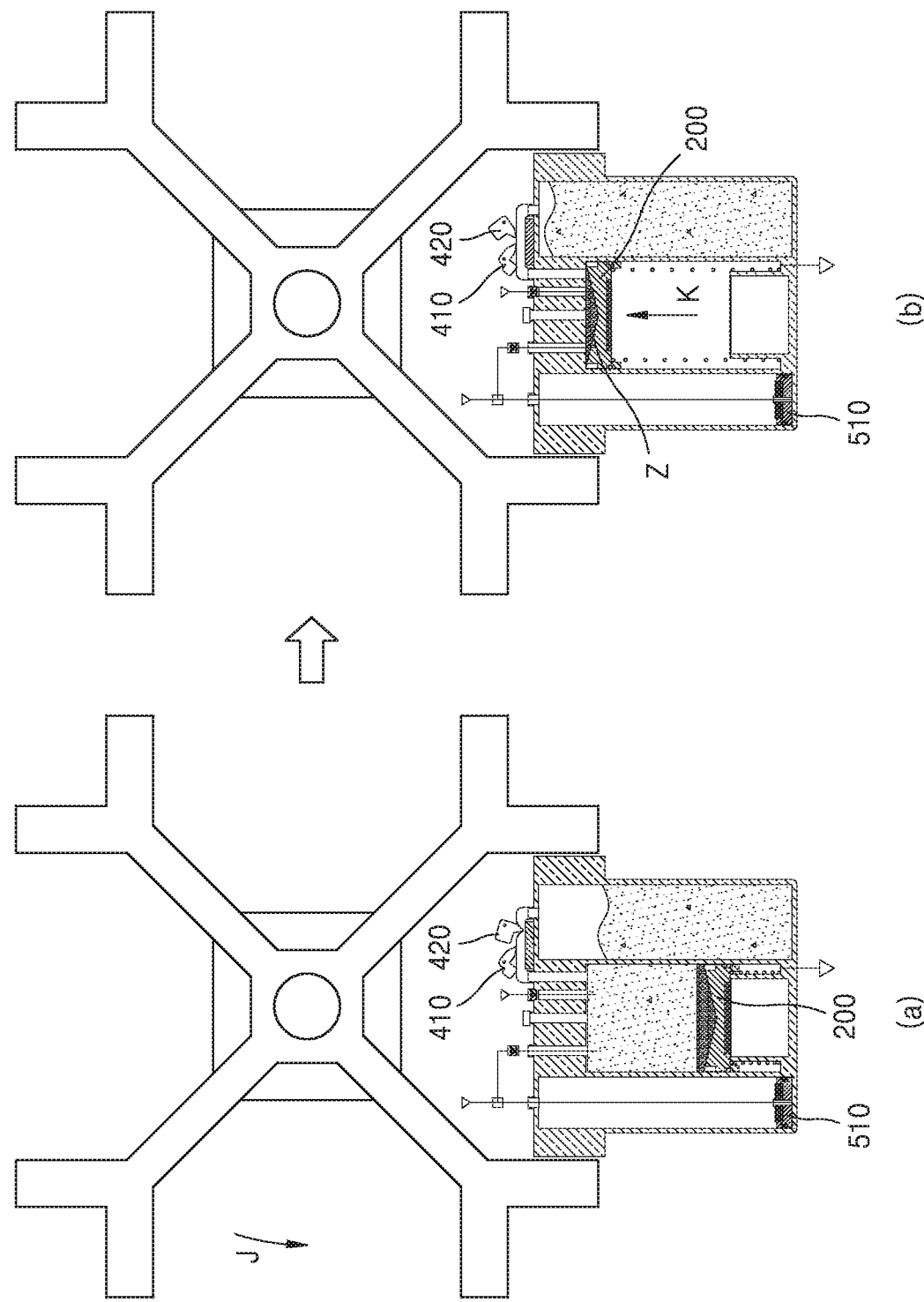

Thereafter, when the first container 100 is again fully filled as shown in (a) of FIG. 27, the movement target material may be no longer injected to the inside of the first container 100, and third centrifugation may be performed. At this time, the centrifugal separator may continue to rotate or accelerate as necessary, in a direction indicated by an arrow J. At this time, the material remaining in the first container 100 and the movement target material may be again mixed, washed, and separated. At this time, the first control valve 400 may be in a closed state.

Thereafter, when the centrifugal separator stops rotating or decelerates as shown in (b), the movement target material filled in the first container 100 may be again discharged through the first connecting duct 402.

During discharging, a centrifugal force may be applied so that a heaviest material may remain in the recessed surface 211 of the first piston 200.

By repeating the process, unnecessary materials in the body fluids and tissue filled in the first container 100 may be discharged to the second container 102 together with the movement target material, and an extract Z that needs to be extracted may be extracted with high purity. Particularly, a material of relatively high mass, such as adipose-derived stem cell, may be maintained to be separated adjacent to the first piston 200 by receiving the centrifugal force during the centrifugation process. Therefore, the material may be not discharged together with the movement target material during the washing and discharging process, and only the unnecessary materials, etc. may be discharged together with the movement target material. Also, since the process is performed without any intervention during the centrifugation, the centrifugation may be easily performed. When the centrifugation is completed, the third opening cap 126 may open to extract a final material through the third opening 124.

While the present disclosure has been shown and described above in regard of preferred embodiments, the present disclosure is not limited to the above-described embodiments, various modifications may be made by one of ordinary skill in the art without departing from the gist of the present disclosure disclosed in the following claims, and such modifications should not be individually understood from the technical concepts or prospects of the present disclosure.

The invention claimed is:

1. A centrifugal separation container for separating a material from tissue and body fluids using a centrifugal force, comprising:
   a first container;
   a second container;
   a first piston positioned in the inside of the first container and configured to be movable up and down in the inside of the first container;
   an elastic body positioned below the first piston in the inside of the first container and configured to elastically bias the first piston upward;
   a first connecting duct having one end connected to the first container and the other end connected to the second container; and
   a first control valve operating by a centrifugal force and configured to open and close the first connecting duct;
   wherein the first control valve comprises a first valve configured as an initial close valve that is closed before a centrifugal force is applied and that is opened after a centrifugal force is applied,
   wherein the first connecting duct comprises a first duct connected to the first container, a second duct connected to the second container, and a vertical flow path connecting the first duct to the second duct and extending vertically, and
   wherein the first control valve comprises a weight body having a predetermined weight and an elastic ring disposed around the weight body, the first control valve closing the vertical flow path before a centrifugal force is applied as the weight body is friction-fitted in the vertical flow path, and after a centrifugal force is applied, escaping from the vertical flow path so that an open state is maintained between the first duct and the second duct, a valve operating hole is formed above the first container to extend vertically, the valve operating hole being located above the vertical flow path, and an operating beam is provided on the weight body to pass the valve operating hole to be exposed upward.

2. The centrifugal separation container of claim 1, wherein the centrifugal force has a component for moving the first piston toward the bottom portion of the first container from the top portion of the first container.

3. The centrifugal separation container of claim 1, wherein the first control valve further comprises a second valve configured as a normal open valve that is opened when no centrifugal force is applied and that is closed when a centrifugal force is applied.

4. The centrifugal separation container of claim 3, wherein at least one part of the first connecting duct is made of a deformable tube.

5. The centrifugal separation container of claim 4, wherein the second valve comprises:
   a second valve body made of a material having a predetermined weight; and
   a second rotation shaft to which the second valve body is rotatably connected, the second rotation shaft spaced from a center of gravity of the second valve body,
   wherein, when a centrifugal force is applied to the second valve body, the second valve body rotates on the second rotation shaft to press and deform at least one part of the first connecting duct to close the first connecting duct.

6. The centrifugal separation container of claim 1, further comprising a stopper formed in the shape of a predetermined block and having a groove into which the operating beam is inserted, the stopper being detachable from the operating beam,
   wherein a predetermined support step is provided at a top end of the operating beam, and by inserting the operating beam into the groove to support the support step by the stopper from below, a position of the weight body is fixed.

7. The centrifugal separation container of claim 1, wherein at least one part of the first connecting duct is made of a deformable tube, and the first control valve further comprises a rotation valve,
   wherein the rotation valve comprises:
   a valve hammer including a valve rod having a predetermined length, a pressing head formed at one end of the valve rod, located above the first connecting duct, and having a predetermined weight, and a rotation shaft disposed at the other end of the valve rod, the valve hammer configured to be rotatable on the rotation shaft; and
   a valve elastic member configured to elastically bias the pressing head upward.

8. The centrifugal separation container of claim 1, further comprising:
   a third container;
   a second piston positioned in the inside of the third container and configured to be movable up and down in the inside of the third container; and
   a second connecting duct connecting the third container with the first container.

9. The centrifugal separation container of claim 8, further comprising a second control valve configured to open and close the second connecting duct,
   wherein the second connecting duct comprises a first line and a second line,
   the third container has an entrance hole formed above the second piston,
   the second piston is in close contact with an inner side surface of the third container, has a predetermined weight, and has a vertical through hole penetrating the second piston body vertically,
   the first line passes through the entrance hole and has one end connected to the second control valve and the other end connected to the vertical through hole, and the second line has one end connected to the second control valve and the other end connected to the first container.

10. The centrifugal separation container of claim 8, wherein the second piston further comprises a weight body having a predetermined weight.

11. A method for moving substances inside a centrifugal separation container, the method comprising:
   providing the centrifugal separation container, the centrifugal separation container comprising:
      a first container having a first space;
      a first piston positioned in the first space, dividing the first space to an upper space and a lower space, and configured to be movable up and down in the inside of the first container;
      a filling container having a filling space in which a movement target material is filled;
      a second piston positioned in the inside of the filling container, dividing the filling space into an upper space and a lower space, and configured to be movable up and down in the inside of the filling container; and
      a connecting duct connecting the first container to the filling container and having one end connected to the lower space below the second piston in the filling container and the other end connected to the upper space above the first piston in the first container; and
   moving a material filled below the second piston in the filling container to the upper space above the first piston in the first container through the connecting duct by applying a centrifugal force to move the second piston and the first piston downward, and to combine positive pressure generated by the second piston with negative pressure generated by the first piston.

\* \* \* \* \*